(12) United States Patent
Musa et al.

(10) Patent No.: US 9,044,623 B2
(45) Date of Patent: Jun. 2, 2015

(54) POLYMER-BOUND UV ABSORBERS IN PERSONAL CARE COMPOSITIONS

(75) Inventors: Osama M. Musa, Hillsborough, NJ (US); Jenn S. Shih, Paramus, NJ (US)

(73) Assignee: ISP Investments Inc., Wilmington, DE (US)

( * ) Notice: Subject to any disclaimer, the term of this patent is extended or adjusted under 35 U.S.C. 154(b) by 538 days.

(21) Appl. No.: 12/694,647

(22) Filed: Jan. 27, 2010

(65) Prior Publication Data

US 2010/0189661 A1 Jul. 29, 2010

Related U.S. Application Data

(60) Provisional application No. 61/147,496, filed on Jan. 27, 2009.

(51) Int. Cl.
| | | |
|---|---|---|
| *A61K 8/30* | (2006.01) | |
| *A61K 9/72* | (2006.01) | |
| *A61Q 17/04* | (2006.01) | |
| *C08G 67/04* | (2006.01) | |
| *A61K 8/81* | (2006.01) | |
| *C08F 8/30* | (2006.01) | |

(52) U.S. Cl.
CPC .............. *A61Q 17/04* (2013.01); *A61K 8/8164* (2013.01); *A61K 2800/57* (2013.01); *C08F 8/30* (2013.01)

(58) Field of Classification Search
CPC ..... C08F 8/30; C08F 222/06; A61K 2800/57; A61K 8/8164; A61Q 17/04
USPC ................ 524/458; 526/262, 264; 424/40, 59
See application file for complete search history.

(56) References Cited

U.S. PATENT DOCUMENTS

| | | |
|---|---|---|
| 2,769,804 A | 11/1956 | Hanson |
| 2,961,347 A | 11/1957 | Floyd |
| 2,971,939 A | 2/1961 | Baer |
| 2,989,517 A | 6/1961 | Hanson |
| 3,227,615 A | 5/1962 | Korden |
| 3,483,276 A | 12/1964 | Mahlman |
| 3,428,589 A | 2/1969 | Coats et al. |
| 3,509,110 A | 4/1970 | Diguilio |
| 3,589,578 A | 6/1971 | Kamphausen |
| 4,077,441 A | 3/1978 | Rosen et al. |
| 4,131,576 A | 12/1978 | Iovine et al. |
| 4,850,517 A | 7/1989 | Ter Stege |
| 4,857,596 A | 7/1989 | Ter Stege |
| 4,868,246 A * | 9/1989 | MacLeay et al. ............. 525/142 |
| 4,975,494 A | 12/1990 | Kamath et al. |
| 5,322,898 A * | 6/1994 | Chaudhuri et al. ........... 525/183 |
| 6,255,405 B1 | 7/2001 | Kang et al. |
| 6,492,455 B1 | 12/2002 | Nadolsky |
| 7,361,710 B2 | 4/2008 | Thames et al. |
| 2005/0191250 A1* | 9/2005 | Harichian et al. .............. 424/59 |
| 2007/0110686 A1* | 5/2007 | Lowe et al. ..................... 424/59 |

OTHER PUBLICATIONS

Medial-dictionary. The free dictionary, meradimate, 2012.*

* cited by examiner

*Primary Examiner* — Johann R Richter
*Assistant Examiner* — Anna Falkowitz
(74) *Attorney, Agent, or Firm* — Thompson Hine LLP; William J. Davis

(57) ABSTRACT

Personal care compositions comprising a polymer-bound UV absorber are described that provide enhanced properties, including customizable UV spectrum protection, broad-spectrum UV spectrum protection, water resistance, and labile UV stabilization. The polymer comprises anhydride functionality, such as maleic anhydride or a derivative thereof, and the UV absorber contains at least one hydroxyl, primary amine, or secondary amine group.

The personal care compositions may be used to treat and/or protect against burns, cancers, erythema, lentigo ("liver spots"), keratotic lesions, wrinkles, and cellular changes of the skin; and/or color changes, embrittlement, lack of luster, tangles, split ends, and/or unmanageability of the hair.

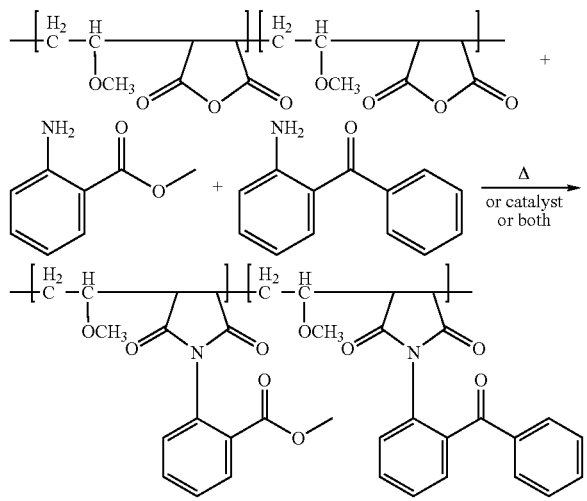

12 Claims, No Drawings

POLYMER-BOUND UV ABSORBERS IN PERSONAL CARE COMPOSITIONS

FIELD OF THE INVENTION

The current invention relates to personal care compositions having a polymer-bound ultraviolet (UV) absorber. In a first embodiment the polymer-bound UV absorbers comprise at least one unit having the structure:

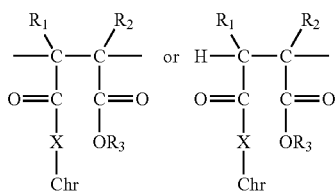

wherein:
(a) Chr-X is the residue of a UV absorber, wherein X is a constituent of said UV absorber and is selected from the group consisting of O and NH; (b) $R_1$ and $R_2$ are independently selected from the group consisting of: hydrogen, halogen atoms, alkyl groups, alkenyl groups, cycloalkyl groups, and aryl groups; (c) $R_3$ is selected from the group consisting of: hydrogen, metal atoms, and organic amine groups; and (d) wherein C— indicates a covalent bond from the shown structure to a polymer backbone or side chain.

In a second embodiment of the invention, the personal care composition comprises a polymer-bound UV absorber comprising at least one unit having the imide form of the above structures when X is NH:

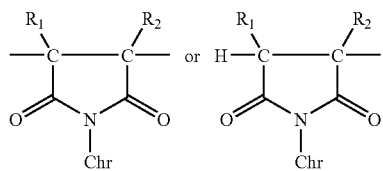

wherein:
(a)

is the residue of a UV absorber; (b) $R_1$ and $R_2$ are independently selected from the group consisting of: hydrogen, halogen atoms, alkyl groups, alkenyl groups, cycloalkyl groups, and aryl groups, and (c) wherein C— indicates a covalent bonded from the shown structure to a polymer backbone or side chain.

The recurring units occur as part of the polymer backbone, on side chains, as pendant groups, or combinations thereof. Homopolymers and non-homopolymers that comprise structures are contemplated.

DESCRIPTION OF RELATED ART

It is now generally accepted that ultraviolet (UV) radiation can be a serious health hazard. Even a limited exposure to solar radiation can cause short- and long-term skin damage, such as erythema, burns, wrinkles, lentigo ("liver spots"), skin cancers, keratotic lesions, and other cellular changes. There is a greater risk for developing such conditions for those who send prolonged time in the sun, such as for their occupation or during recreation.

UV radiation is just one portion of the electromagnetic spectrum with wavelengths from about 100 nm and about 400 nm, and is further divided into three subregions. UV-A radiation, from about 320 nm to about 400 nm, has the longest wavelength within the UV spectrum, and consequently is the least energetic. While UV-A rays can induce skin tanning, they are liable to induce adverse changes as well, especially in the case of sensitive skin or of skin which is continually exposed to solar radiation. In particular UV-A rays cause a loss of skin elasticity and the appearance of wrinkles, leading to premature skin aging. UV-B rays have shorter wavelengths, from about 290 nm to about 320 nm, and their higher energy can cause erythema and skin burns which may be harmful. The third subgroup, UV-C has the shortest wavelengths, from about 200 nm to about 290 nm, and the highest energy. The Earth's ozone layer effectively filters much UV-C radiation from reaching the ground. Nonetheless, UV-C rays can be generated from tanning bed devices.

In addition to harming the skin, UV radiation can injure the hair, resulting in color changes (especially for color-treated hair), embrittlement, and a loss in aesthetics (e.g., shine, manageability).

UV radiation damage is not limited to the skin and hair, as inanimate objects exposed to solar radiation can experience changes related to color, hardness, and structural integrity, which can contribute to aesthetical and functional deterioration. Thus, there is the very real and demanding need for compositions that protect the skin, hair, and objects from UV rays, especially UV-A and UV-B radiation. Of special interest are compositions that provide broad UV-spectrum protection from both UV-A and UV-B radiation.

Broadly speaking, para-aminobenzoic acid (PABA) exhibits a common trait shared with many UV absorbers/filters. The molecule possesses both electron withdrawing and electron accepting groups, providing resonance delocalization that coincides with the absorbed energy of UV radiation:

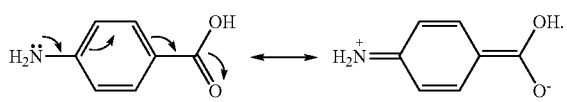

However, PABA is a highly polar molecule, making it water soluble, and giving it low persistence, meaning that it is not highly retained on the skin after swimming or perspiring. In addition, due to extensive intermolecular bonding, PABA exists as a solid, which may further complicate its formulation. Thus, there exists the need to improve the persistence of UV absorbers, especially those that are water-soluble, and to provide formulation flexibility.

UV absorbers may exhibit photolability, in which the absorbed energy causes photodegradation and/or photoreactivity, and thus reduce its efficacy. Such photolability may result from irreversible isomerisms (i.e., keto-enol tautomerism and cis-trans isomerism), photocleavage, and/or photoaddition, and may be formulation sensitive, (e.g., blends of avobenzone and octinoxate). Examples of photolabile UV absorber include, without limitation: avobenzone, PABA derivatives, cinnamates, and dibenzoyl methane derivatives, all of which degrades over time, and reduce UV protection. Hence, there exists a need to stabilize UV absorbers from photodegradative effects.

Additionally, there exists the need to enhance the efficacy of UV absorbers without increasing their content in the formula, since a maximum addition level frequently is regulated. This efficacy need is especially important for avobenzone, a highly effective UV-A absorber. Avobenzone is subject to keto-enol isomerization due to formulation dependencies (e.g., solvent, other UV absorbers):

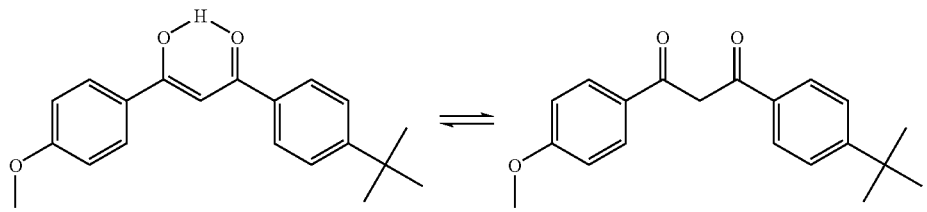

The enol tautomer (left) has its maximum absorbance at 357 nm, which identifies it as a UV-A absorber. Unfortunately, avobenzone is subject to bimolecular reactions (viz, via cleavage mechanisms) that alter the molecule's structure and decrease its effectiveness as an UV absorber. Hence, an effective method is needed for stabilizing labile chromophores like avobenzone in order to enhance their efficacy without increasing their addition level.

Methods for stabilizing chromophores, and in particular UV absorbers, are known in the prior art. For example, Japanese patent 1971/26,860 describes UV stabilizers having amino, hydroxyl, or isocyanate groups attached to crosslinked polymers, being crosslinked glycidyl methacrylate-divinylbenzene copolymers or crosslinked styrene-maleic anhydride-divinylbenzene copolymers.

U.S. Pat. No. 4,868,246 teaches polymer chemistries having UV absorbers bonded to recurring units:

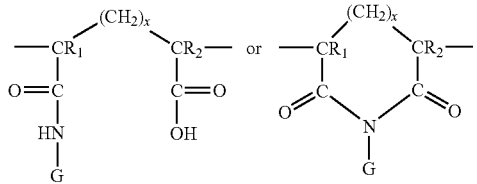

in the polymer backbone, on grafted side chains, as pendant units, or as combinations thereof. The group N-G is the residue of a primary amino or hydrazido substituted stabilizer group selected from (a) 2-hydroxybenzophenones, (b) 2-(2-hydroxyphenyl)-2H-benzotriazoles, (c) aryl salicylates, or (d) oxalic acid amides. The polymeric stabilizers are directed for use in other polymeric systems which are normally subject to actinic light degradation, for example polypropylene. No mention is made of their use in personal care compositions.

A similar approach is taught in U.S. Pat. No. 4,857,596 for thermally stabilizing antioxidants.

Polymer-bound light stabilizers are disclosed in U.S. Pat. No. 4,975,494 that are prepared from a preformed polymer having two different types of reactive groups and a light stabilizer having hydrazido functionality.

U.S. Pat. No. 6,569,531 teaches additive-containing resins having a bi- or multifunctional additive linking a polyester resin with an additive, such as a UV absorber.

Japanese patent 1985/84,378 provides 2-hydroxy-4-(2-hydroxyethoxy)benzophenone reacted with maleic anhydride-grafted polyethylene to form a polyethylene-bound 2-hydroxybenzophonone semi-ester.

Two radiation-absorbing polymer chemistries are taught in U.S. Pat. No. 6,255,405. The '405 patent is directed toward radiation-absorbing compositions and coatings, particular for "forming a bottom anti-reflective coating upon producing an integrated circuit." The polymeric compositions comprise two recurring units, the first having the formula:

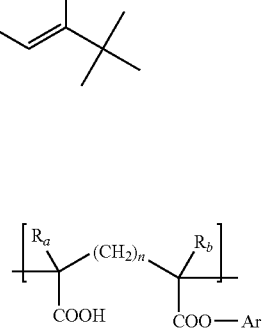

wherein $R_a$ and $R_b$ may be the same or different and represent hydrogen, an alkyl group or other organic groups, Ar represents an organic chromophore, and n represents 0 or an integer of 1 or more; and the second recurring unit having the formula:

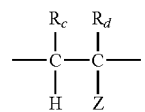

wherein $R_c$ and $R_d$ may be the same or different and each represents hydrogen, an alkyl group, a carboxyl group, or other organic groups, and Z represents hydrogen, a substituted or non-substituted alkoxyl group, a substituted or non-substituted alkyl group, a halogen atom, —CN, an alkylcarbonyloxy group, an imide group, a substituted or non-substituted carbamoyl group, a substituted or non-substituted oxycarbonyl group, or a substituted or non-substituted phenyl group.

U.S. Pat. No. 6,492,455 discloses compositions comprising the reaction product of a $C_6+$ alpha olefin/maleic anhydride copolymer with a polyfunctionalized secondary or tertiary amine. The resulting copolymer is an alternating copolymer of an olefinic monomer and a maleic anhydride with a polyfunctionalized secondary or tertiary amine. Uses includes hair spray and water-proof sunscreen compositions U.S. Pat. No. 7,361,710 describes compositions comprising the reaction of (a) an unsaturated vegetable oil and an enophile or dienophile having acid, ester, or anhydride functionality and (b) a functional vinyl monomer. For example, soybean oil is reacted with maleic anhydride, to yield a maleated vegetable oil:

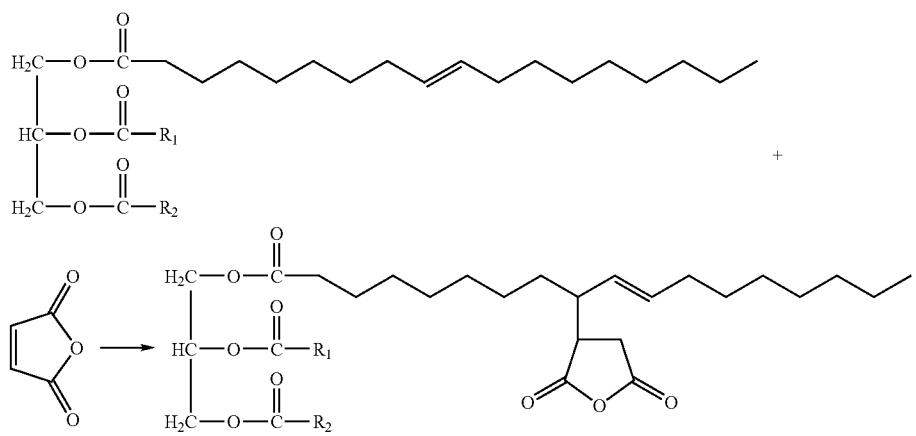

The maleated oil is reacted with hydroxyethyl methacrylate, 2-(tert-butylamino)ethyl methacrylate, or glycidyl methacrylate.

Another maleated oil is described in U.S. Pat. No. 3,428,589, which is directed to polycarboxylic acid anhydride resins of high viscosity, and for such resins of voltage capabilities. This invention discloses the heating (1) of a dry oil, a modified drying oil, or a mixture thereof, and (2) and alpha, beta-ethylenically unsaturated dicarboxylic acid anhydride, which is heated until a polycarboxylic acid anhydride resin product (i.e., an adduct) with a desirably high viscosity is obtained. The polycarboxylic acid anhydride resin is then reacted with an organic aromatic primary or secondary amine, as represented in the following reaction:

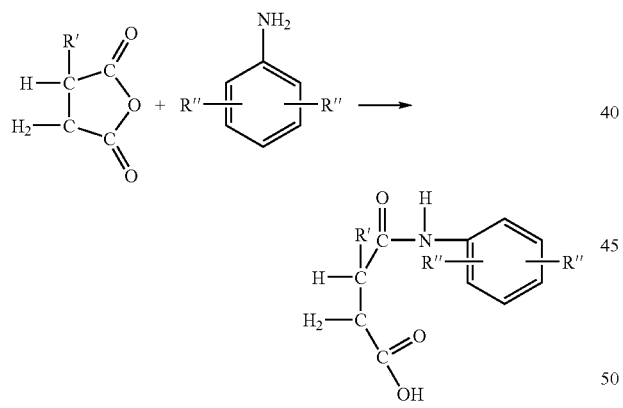

wherein R' represented the drying oil portion of the adduct, and R" is hydrogen or alkyl. The '589 patent specifies that the organic aromatic primary or secondary amine has from 1 to 20 carbon atoms, preferably from 1 to 10 carbon atoms. The '589 patent discloses compositions for electrocoating baths, compositions with high throwing power, and of excellent intermediate voltage capacity.

Additional disclosure related to anhydride-functionalized vegetable oils is provided by Aydin, S., et al., *Prog Org Coat*, 51, 273-279, 2004; and by Guner, F. S., et al., *Prog Polym Sci*, 31, 633-670, 2006, both of which are incorporated in their entirety by reference. While these works describe methods to graft anhydride functional groups onto vegetable oils, they do not teach subsequent grafting of UV absorbers onto the anhydride moiety.

Functionalized poly(alpha olefin-maleic anhydride) polymers are the subject of application WO 2007/096400A1. This functionalized copolymer has the structure:

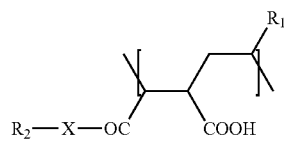

wherein X is —O— or —NH—, and —X—$R_2$— is a functional radical selected from a group that includes natural molecules that are UV absorbers, such as tannins, flavonoids, thymol, caffeic acid esters, and vitamin E.

Despite advances in designing UV absorbers and in developing formulation blends, there remains a commercial demand for UV absorber compositions with boosted performance, especially for single compositions that provide full UV-spectrum protection, enhanced water-resistance, reduced tendency for skin penetration, and improved stability especially for labile UV absorbers. The compositions disclosed herein uniquely accomplish these properties.

SUMMARY OF THE INVENTION

It has been discovered that personal care compositions with decreased UV absorber migration, decreased skin penetration, and enhanced UV absorber performance are those compositions with polymer-bound UV absorber(s) comprising at least one unit having the structure:

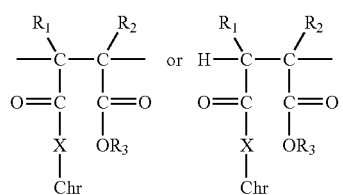

wherein:
(a) Chr-X is the residue of a UV absorber, wherein X is a constituent of said UV absorber and is selected from the group consisting of O and NH; (b) $R_1$ and $R_2$ are independently selected from the group consisting of: hydrogen, halogen atoms, alkyl groups, alkenyl groups, cycloalkyl groups, and aryl groups; (c) $R_3$ is selected from the group consisting of: hydrogen, metal atoms, and organic amine groups; and (d) wherein C— indicates a covalent bond from the shown structure to a polymer backbone or side chain.

Another embodiment of the invention relates to personal care compositions with polymer-bound UV absorber(s) comprising at least one unit of the imide form of the above structures when X is NH:

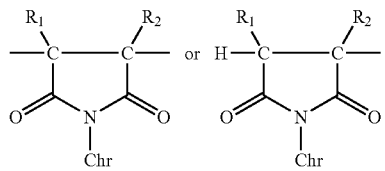

wherein:
(a)

is the residue of a UV absorber; (b) $R_1$ and $R_2$ are independently selected from the group consisting of: hydrogen, halogen atoms, alkyl groups, alkenyl groups, cycloalkyl groups, and aryl groups, and (c) wherein C— indicates a covalently bond from the shown structure to a polymer backbone or side chain.

The recurring units occur as part of the polymer backbone, on side chains, as pendant groups, or combinations thereof. Homopolymers and non-homopolymers that comprise structures are contemplated.

The described compositions have at least one polymer-bound UV absorber that exhibits UV-A, UV-B, or UV-C activity, more preferably UV-A or UV-B activity. In preferred embodiments of the invention, the polymer exhibits both UV-A and UV-B absorption activity. In this manner more than one UV absorber may be covalently bonded to the polymer backbone and/or side chains, and/or as grafted pendants. The advantage of doing so is to boost the performance of more than one UV absorber in a single molecule, especially one or more UV-A absorbers and one or more UV-B absorbers.

With proper selection of the polymer backbone, side chains, branching, and/or grafted pendants, the polymer molecular weight and molecular weight distribution, and the UV absorber(s), the described compositions exhibit a number of properties that make them desirable personal care applications, such as: better water resistance or water proofness, and customizable UV spectrum protection (especially in one molecule). The stabilization of labile UV absorbers, such as avobenzone, may be stabilized when blended with these compositions, thus further increasing their use as well.

In an especially preferred embodiments, the personal care compositions of the invention are sun care compositions.

DETAILED DESCRIPTION OF PREFERRED EMBODIMENTS

The terms ultraviolet and UV are taken to mean electromagnetic radiation, especially solar electromagnetic radiation, with a wavelength from about 100 nm to about 400 nm, and includes the UV-A, UV-B, and UV-C subclassifications of such radiation.

The term UV-A means ultraviolet electromagnetic radiation with a wavelength from about 320 nm to about 400 nm, and includes UV-A1 (from about 340 nm to about 400 nm) and UV-A2 (from about 320 nm to about 340 nm).

The term UV-B means ultraviolet electromagnetic radiation with a wavelength from about 290 nm to about 320 nm.

The term UV-C means ultraviolet electromagnetic radiation with a wavelength from about 200 nm to about 290 nm.

The term UV absorber is taken to mean a chemical entity that absorbs, scatters, and/or reflects electromagnetic radiation. Preferred UV absorbers are those that absorb, scatter, and/or reflect X-rays, UV radiation, visible light, infrared radiation, and/or microwave radiation. Suitable UV absorbers include those approved for human use (e.g., for application to the skin and hair).

The symbol C— (without a molecule or group indicated at the end of the dash) means a covalent bond between the indicated carbon atom and a polymer backbone, side chain, or grafted pendant.

The term monomer refers to the repeat units that comprise a polymer. A monomer is a compound that chemically bonds to other molecules, including other monomers, to form a polymer.

The term polymer refers to a molecule comprising one or more monomer unit types connected by covalent chemical bonds. By this definition polymer encompasses molecules wherein the number of monomer units ranges from very few, which more commonly may be called oligomers, to very many. Nonlimiting examples of polymers include homopolymers, non-homopolymers, copolymers, terpolymers, tetramers, and the like, wherein the polymer is a random, blocked, or alternating polymer.

The term homopolymer refers to a molecule that consists essentially of a single monomer type.

The term non-homopolymer refers to a molecule that comprises more than one monomer types.

The term copolymer refers to a non-homopolymer that comprises two different monomer types.

The term terpolymer refers to a non-homopolymer that comprises three different monomer types.

The term branched refers to any non-linear molecular structure. To avoid any arbitrary delineation, the term branched describes both branched and hyperbranched structures.

The term polymer-bound UV absorber refers to a polymer molecule having at least one covalently-bonded UV absorber bound to the polymer backbone, side chain, or grafted pendant.

The term free radical addition polymerization initiator refers to a compound used in a catalytic amount to initiate a free radical addition polymerization. The choice of initiator depends mainly upon its solubility and its decomposition temperature.

The term personal care composition refers to compositions intended for use on or in the human body, such as skin, sun, oil, hair, cosmetic, and preservative compositions, including those to alter the color and appearance of the skin and hair. Potential personal care compositions include, but are not limited to, compositions for increased flexibility in styling, durable styling, increased humidity resistance for hair, skin, and color cosmetics, sun care water-proof/resistance, wear-resistance, and thermal protecting/enhancing compositions.

The term sun-care formulation means personal care and/or pharmaceutical compositions and formulations comprising an effective amount of UV-absorbing compositions. Sun-care formulations include beach and non-beach products that are applied to the face, décolleté, lips, and skin to treat and/or protect against erythema, burns, wrinkles, lentigo ("liver spots"), skin cancers, keratotic lesions, and cellular changes of the skin; and to hair to treat and/or protect against color changes, lack of luster, tangles, split ends, unmanageability, and embrittlement.

All percentages, ratio, and proportions used herein are based on a weight basis unless other specified.

Characteristic Unit

As mentioned earlier, personal care compositions of the invention have at least one polymer-bound UV absorber that comprises at least one unit having the structure:

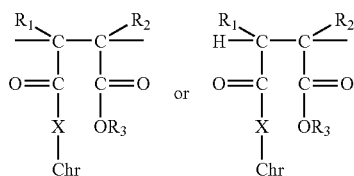

wherein:
(a) Chr-X is the residue of a UV absorber, wherein X is a constituent of said UV absorber and is selected from the group consisting of O and NH; (b) $R_1$ and $R_2$ are independently selected from the group consisting of: hydrogen, halogen atoms, alkyl groups, alkenyl groups, cycloalkyl groups, and aryl groups; (c) $R_3$ is selected from the group consisting of: hydrogen, metal atoms, and organic amine groups; and (d) wherein C— indicates a covalent bond to a polymer backbone or side chain.

In preferred embodiments, $R_3$ is hydrogen.

Another embodiment of the invention relates to personal care compositions of polymer-bound UV absorber(s) comprising at least one unit of the imide form of the above structures when X is NH:

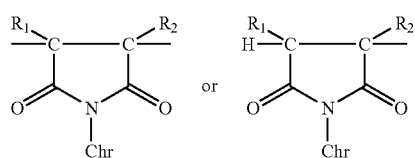

wherein:
(a)

is the residue of a UV absorber; (b) $R_1$ and $R_2$ are independently selected from the group consisting of: hydrogen, halogen atoms, alkyl groups, alkenyl groups, cycloalkyl groups, and aryl groups, and (c) wherein C— indicates a covalent bonded to a polymer backbone or side chain.

The polymer having the polymer-bound UV absorber(s) having the abovedescribed unit structures can be produced by one of three methods. In the first method, a polymer having at least one unsaturated carbon-carbon double bond is ene graft reacted with an unsaturated anhydride molecule. Examples of suitable unsaturated polymers include, without limitation, the homopolymers and non-homopolymers of isoprene, butadiene, and partially conjugated dienes. These polymers include those disclosed in WO 01/26620, which hereby is incorporated in its entirety by reference.

Suitable unsaturated anhydrides also are known, and include maleic anhydride and its derivatives (e.g., methyl maleic anhydride, dimethyl maleic anhydride, tetrahydrophthalic anhydride, and himic anhydride), and citraconic anhydride and its derivatives. Following or concurrent to the unsaturated anhydride ene graft reaction, a UV absorber having at least one hydroxyl, primary amine, or secondary amine group is reacted to open the anhydride ring and create the auric acid form of the structures presented earlier.

Various polymers of conjugated dienes and copolymers of conjugated dienes and vinyl aromatic hydrocarbons may be used. Polymers of conjugated dienes include polymers derived from one or more conjugated diene monomers. Thus, polymers derived from a single conjugated diene such as 1,3-butadiene (i.e., a homopolymer) or polymers derived from two or more conjugated dienes such as, for example, 1,3-butadiene and isoprene or 1,3-butadiene and 1,3-pentadiene (i.e., a copolymer) and the like may be utilized. Copolymers which may be hydrogenated include random copolymers of conjugated dienes and vinyl aromatic hydrocarbons and block copolymers of conjugated dienes and vinyl aromatic hydrocarbons which exhibit elastomeric properties.

One such exemplary unsaturated polymer is polybutadiene and its derivatives, produced by polymerizing 1,3-butadiene. The polymerization of 1,3-butadiene can produce three different conformations, 1,2-vinyl

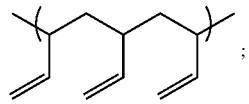

1,4-trans:

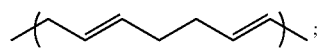

and 1,4-cis:

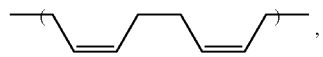

and all three conformations may be retained in varying amounts in commercially available polybutadiene.

A second method for the synthesis of the polymer-bound UV absorber is a variation of the first method, wherein the polymer has the anhydride functional group pendant to the polymer backbone, i.e., the polymer already has been ene graft reacted with one or more anhydride groups. These anhydride-functionalized polymers may be custom-prepared for the use of making the polymer-bound UV absorbers for personal care compositions, or it may be sufficient to purchase an anhydride-functionalized polymer. Preparation of anhydride-functionalized polymers for use described here include customization of the polymer properties, such as polymer molecular weight and molecular weight distribution, anhydride content, anhydride type.

Like their polybutadiene counterparts, anhydride-functionalized polybutadienes, especially maleated polybutadienes, are commercially available for purchase. Examples include the Ricon® 130 MA8, 130 MA13, 130 MA20, 131 MA5, 131 MA10, 131 MA17, 131 MA20, 156 MA17, and 184 MA6 product lines offered for sale by Sartomer Company, Inc. (Exton, Pa.). The Ricon® maleated polybutadiene family of polymers contains a relatively high amount of the 1,2-vinyl conformation. The different Ricon® grades offer a range of number-average molecular weight ($<M_n>$) and succinic anhydride groups per chain (Table 1). The polybutadiene backbone imparts moisture resistance, while increasing chain length between succinic anhydride function groups increases hydrophobicity and hardness.

TABLE 1

Maleated polybutadiene product lines of Sartomer Company, Inc.

| grade | $<M_n>$ (Da) | maleic anhydride groups per chain |
|---|---|---|
| 130 MA8 | 2700 | 2 |
| 130 MA13 | 2900 | 4 |
| 130 MA20 | 3100 | 6 |
| 131 MA5 | 4700 | 2 |
| 131 MA10 | 5000 | 5 |
| 131 MA17 | 5400 | 9 |
| 131 MA20 | 5600 | 11 |
| 156 MA17 | 2500 | 3 |
| 184 MA6 | 9100 | 6 |

Modified polyolefins also are of interest in this invention, in which one or more anhydride groups are presented in a side chain and/or as a pendant group with respect to the polymer backbone. Any polymer or copolymer comprising ethylene, propylene, or 1-butene groups can be modified to form the anhydride modified polyolefin, such as described in U.S. Pat. No. 3,483,276.

Maleic anhydride adducts of hydrogenated polymers or copolymers are polymeric products containing pendant succinic anhydride groups which are formed by reacting maleic anhydride with hydrogenated polymers of conjugated dienes or hydrogenated copolymers of conjugated dienes and vinyl aromatic hydrocarbons containing a residual unsaturation level of from 0.5% to 20% of their original unsaturation level prior to hydrogenation. The reaction, which is conducted by heating a mixture of the maleic anhydride and hydrogenated polymer or copolymer containing residual unsaturation, proceeds by means of the ene reaction mechanism. The maleic anhydride adds to the unsaturation of the polymer to form the polymer product containing the pendant succinic anhydride groups. This polymer, by virtue of the pendant anhydride groups, can be reacted with stabilizers containing primary amino or hydrazide groups to form the polymer bound stabilizers of the invention.

The amounts of maleic anhydride employed in the reaction can vary considerably depending on the specific nature of the hydrogenated polymer and the properties desired in the final product. In general, the amount of maleic anhydride employed may range from 0.1% to about 25% by weight based on total weight of maleic anhydride and hydrogenated polymer with a preferred amount being from about 0.2% to 5% by weight.

In addition to these first two methods, a third technique is available to create the polymer-bound UV absorber molecules. Unlike the other methods in which the anhydride functional group is pendant to the polymer backbone, in the third method the anhydride group itself forms all or part of the polymer backbone. This description means that the polymer is a homopolymer, copolymer, terpolymer, or non-homopolymer of an anhydride mer. In especially preferred embodiment, this anhydride mer is maleic anhydride or one of its derivatives, such as, but not limited to: methyl maleic anhydride, dimethyl maleic anhydride, and citaconic anhydride. By means of this third method, a UV absorber having at least one hydroxyl, primary amine, or secondary amine group is reacted to open the anhydride ring and form the amic acid structures. Many polymers suitable to this third method are known.

The polymer backbone may be a homopolymer of an anhydride mer, such as poly(maleic anhydride), poly(dimethyl maleic anhydride), poly(methyl maleic anhydride), and poly(citaconic anhydride).

Alternatively, the polymer backbone may be provided by a copolymer. One exemplary member of this polymer class is poly(styrene-co-maleic anhydride), which are a general class of alternating copolymers of styrene and maleic anhydride, or the non-equimolar copolymers containing less than about 50 mole percent of the anhydride monomer. This copolymer is defined by its generic chemical structure:

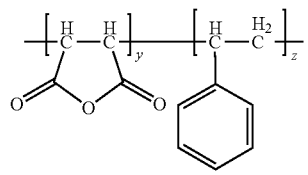

wherein the subscripts y and z represent the molar ratios of the two constituent blocks.

The styrene constituent in poly(styrene-co-maleic anhydride) may be replaced in whole or in part by other vinylaromatic monomers such as α-methylstyrene, nuclear methylstyrenes, ethylstyrene, iso-propylstyrene, tert-butylstyrene, chlorostyrenes, dichlorostyrenes, bromostyrenes, dibromostyrenes, vinylnaphthalene and the like. Similarly, the maleic anhydride can be replaced in whole or in part by another alpha, beta-unsaturated cyclic dicarboxylic acid anhydride such as citraconic, chloromaleic, bromomaleic, dichloromaleic, dibromomaleic, phenylmaleic, and the like. The preferred α, β-unsaturated cyclic anhydride is maleic anhydride. The copolymer also may contain a termonomer such as 1-3 carbons alkyl acrylate or methacrylate, acrylonitrile, methacrylonitrile, acrylamide, methacrylamide, acrylic acid or methacrylic acid, or any of the optional polymerizable groups presented later.

Suitable poly(styrene-co-maleic anhydride) copolymers may be prepared by any of the several methods available for the preparation of styrene-maleic anhydride copolymers or they may be purchased commercially. Non-equimolar copolymers may be prepared by solution polymerization directly from the respective monomers by the incremental addition of the reactive monomer as taught by U.S. Pat. No. 2,971,939, by a continuous recycle polymerization process such as described in U.S. Pat. Nos. 2,769,804 and 2,989,517, by the suspension polymerization process described in U.S. Pat. No. 3,509,110, or by numerous known variations.

A second type of preferred polymer of the third method is a poly(alkyl vinyl ether-co-anhydride), such as poly(methyl vinyl ether-co-maleic anhydride):

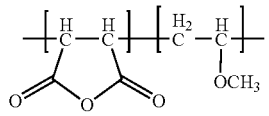

In preferred embodiments of the invention, this copolymer is predominantly alternating poly(methyl vinyl ether-co-maleic anhydride).

Poly(methyl vinyl ether-co-maleic anhydride) is offered for commercial sale as Gantrez® AN by International Specialty Products (Wayne, N.J.).

Regardless of the synthesis approach (method 1, 2, or 3), the imide forms can be created from the amic acid form through the application of heat, the use of a reaction catalyst, or the use of a reaction initiator, or combinations thereof. A consideration of these factors will be given when describing the synthesis of the invention's compositions.

UV Absorber

The polymer-bound UV absorbers for use in the personal care compositions of this invention are those that contain the necessary reactive groups to open the anhydride ring. As was already mentioned, the necessary reactive groups are provided by UV absorbers that comprise at least one hydroxyl, primary amine, and/or secondary amine group.

Due to great activity in developing new absorbers, it outside the scope of this invention to specify every UV absorber approved for personal care use in every country. Rather, this invention recognizes the specific reactive chemistries necessary to produce the claimed compositions.

It also is appreciated by one skilled in the art that UV absorbers most typically exhibit absorptivity across the UV spectrum. For example, this is to say that a UV absorber typically considered to be a UV-A absorber frequently also absorb UV-B radiation, and vice versa. As such, the invention is not limited to UV absorbers that exhibit strictly and solely UV-A or UV-B activity.

Especially preferred UV absorbers are UV-A and UV-B absorbers, since Earth's atmospheric effectively filters much UV-C radiation from reaching the land surface.

Non-limiting examples of UV absorbers approved for human use that exhibit the necessary hydroxyl, primary amine, and/or secondary amine functionalities include:

p-aminobenzoic acid and its derivatives:
4-aminobenzoic acid (PABA); digalloyl triolate; 2,3-dihydroxypropyl 4-aminobenzoate (lisadimate, amyl dimethyl PABA, glyceryl PABA); ethyl-4-bis(hydroxypropyl)-aminobenzoate (roxadimate); ethoxylated ethyl 4-aminobenzoate (PEG-25 PABA); hexyl 2-[4-(diethylamino)-2-hydroxybenzoyl]benzoate (diethylamino hydroxy benzoyl hexylbenzoate); (5-methyl-2-propan-2-ylcyclohexyl) 2-aminobenzoate (menthyl anthranilate, meradimate);

benzophenone derivatives:
(2-hydroxy-4-methoxyphenyl)-(2-hydroxyphenyl)methanone (dioxybenzone, benzophenone-8); 2,2',4,4'-tetrahydroxybenzophenone (benzophenone-2, Uvinul® D-50); 2-hydroxy-4-methoxybenzophenone (oxybenzone, benzophenone-3); 2,2'-dihydroxy-4,4'-dimethoxybenzophenone (benzophenone-6); 2,2'-dihydroxy-4,4'-dimethoxybenzophenone-5,5'-disulphonic acid sodium salt (benzophenone-9); 4-hydroxy-2-methoxy-5-(oxo-phenylmethyl)benzenesulfonic acid (sulisobenzone, benzophenone-4); 2-hydroxy-4-methoxybenzophenone-5-sulphonic acid sodium salt (benzophenone-5), 2-aminobenzophenone;

benzotriazole derivatives:
2-(benzotriazol-2-yl)-6-[[3-(benzotriazol-2-yl)-2-hydroxy-5-(2,4,4-trimethylpentan-2-yl)phenyl]methyl]-4-(2,4,4-trimethylpentan-2-yl)phenol (bisoctrizole); 2-(2-hydroxy-5-methylphenyl)benzotriazole (drometrizole); 2-(2H-benzotriazol-2-yl)-4-methyl-6-[2-methyl-3-(1,3,3,3-tetramethyl-1-((trimethylsilyl)oxy)disiloxanyl)propyl]phenol (drometrizole trisiloxane): 2,2'-methylenebis-[4-(1,1,3,3-tetramethylbutyl)-6-(2H-benzotriazol-2-yl)phenol](methylene bis-benzotriazolyl tetramethylbutylphenol);

benzimidazole derivatives:
2-phenylbenzimidazole-5-sulfonic acid and its potassium, sodium and triethanolamine salts, (phenylbenzimidazole sulfonic acid, ensulizole); 2,2'-(1,4-phenylene)bis-1Hbenzimidazole-4,6-disulfonic acid, monosodium salt (disodium phenyl dibenzimidazole tetrasulfonate);

camphor derivatives:
α-(2-oxoborn-3-ylidene)-toluene-4-sulphonic acid and its salts (benzylidene camphor sulfonic acid); 3,3'-(1,4-phenylenedimethylene)bis(7,7-dimethyl-2-oxobyciclo-[2.2.1]hept-1-ylmethane sulphonic acid and its salts (terephthalylidene dicamphor sulfonic acid, emcamsule); polymer of N-{(2 and 4)-[(2-oxoborn-3-ylidene)methyl]benzyl} (polyacrylamido methylbenzylidene camphor);

cinnamates:
diethanolamine-p-methoxycinnamate (DEA methoxycinnamate);

quinones:
lawsone with dihydroxyacetone;

salicylates:
2-ethylhexyl salicylate (ethylhexyl salicylate); 3,3,5-trimethylcyclohexyl salicylate (homosalate, homomethyl salicylate); 2-(bis(2-hydroxyethyl)amino)ethyl 2-hydroxybenzoate (trolamine salicylate, triethanol amine salicylate);

triazine derivatives:
2,4,6-trianilino-(p-carbo-2'-ethylhexyl-1'-oxy)-1,3,5-triazine (ethylhexyl triazone); 4,4'-[[6-[[[(1,1-dimethylethyl)amino]carbonyl]phenyl]amino]-1,3,5-triazine-2,4-diyl]diimino]bis-bis(2-ethylhexyl)benzoate (diethylhexyl butamido triazone, iscotrizinol); 2,2'-[6-(4-methoxyphenyl)-1,3,5-triazine-2,4-diyl]bis[5-[(2-ethylhexyl)oxy]phenol (bis-ethylhexyloxyphenol methoxyphenyl triazine); and 2,2'-[6-(4-methoxyphenyl)-1,3,5-triazine-2,4-diyl]bis{5-[(2-ethylhexyl)oxy]phenol}(bemotrizinol, Tinosorb® S).

The abovementioned UV absorbers having at least one hydroxyl, primary amine, or secondary amine group generally contain 10 carbon atoms or more, and preferably contain 20 carbon atoms or more.

Preferred embodiments of this invention are compositions comprising at least one UV-A active, including, but not limited to: 2-aminobenzophenone, bemotrizinol, bis-benzoxazoyl phenyl ethylhexyl amino triazine, bisoctrizole, diethylaminohydroxybenzoylhexylbenzoate, diethylhexyl butamido triazone, dioxybenzone, disodium phenyl dibenzimidazole tetrasulfonate, drometrizole trisiloxane, ecamsule, ensulizole, menthyl anthranilate, meradimate, oxybenzone, and sulisobenzone.

Also preferred embodiments of this invention are compositions comprising at least one UV-B active, including, but not limited to: aminobenzoic acid, amyl dimethyl PABA, benzophenone-9,3-benzylidene camphor sulfonic acid, bisoctrizole, camphor benzalkonium methosulfate, diethanolamine p-methoxycinnamate, diethylhexyl butamido triazone, digalloyl trioleate, drometrizole trisiloxane, ensulizole, ethyl 4-bis(hydroxypropyl)aminobenzoate, ethylhexyl p-methoxycinnamate, 2-ethylhexyl salicylate, ethylhexyl triazone, glyceryl aminobenzoate, homomethyl salicylate, lawsone with dihydroxyacetone, meradimate, methoxycinnamido propyl hydroxy sultaine, oxybenzone (benzophenone-3), 2-phenylbenzimidazole-5-sulfonic acid (and its potassium, sodium and triethanolamine salts), sulisobenzone (benzophenone-4), and triethanolamine salicylate.

In especially preferred embodiments of this invention, the personal care composition comprises a polymer-bound UV absorber having UV-A absorption activity and UV-B absorption activity. To achieve this dual UV absorptivity activity, a single UV absorber having both UV-A and UV-B absorptivity may be reacted. Alternatively, at least one UV-A absorber and at least one UV-B absorber may be reacted onto the same or different polymers. Within the context of this embodiment, it is especially preferred that at least one UV-A absorber and at least one UV-B absorber are reacted onto the same polymer to create a polymer molecule with both UV-A and UV-B absorbing activity.

Synthesis of the UV Absorber Composition

The reaction may be carried out for times ranging from 30 seconds to 48 hours or even more, depending upon (a) the degree of conversion to imide form that is desired, (b) the reactivity of the UV absorber(s), (c) the reaction temperature employed, (d) the presence or absence of a solvent, and (e) the use or non-use of an initiator and/or catalyst. With the use of an optional reaction solvent or solvents, it may be preferred to remove the solvent(s) after the reaction, e.g., at reduced pressure and/or elevated temperature, and then to add a different solvent conducive to the final formulation.

Typically, the temperature ranges from 20° C. to the decomposition temperature of any reactant. At lower reaction temperatures, UV absorber bearing primary and/or secondary amine group may become attached to the anhydride coupling agent as amic acid derivatives. During high-temperature processing, imidization of the amic acid form may occur. In preferred embodiments, imidization does occur, resulting in the presented imide structures.

Within one embodiment of the invention it is desirable to employ mixtures of UV absorbers (e.g., UV-A and UV-B absorbers). It may be advantageous to add the least reactive absorbers first, and the more reactive ones later in the preparation.

Alternately, multiple UV absorbers can be blended together and used. Regardless of the type or number of UV absorbers, their total molar equivalents should not exceed the equivalents of the anhydride moiety in the composition. As necessary, additional reactive species can be attached to the composition. To properly adjust the stoichiometry of multiple reactive additives, the relative anhydride content must be considered. Typically, the molecular weight of the polymeric UV absorber composition ranges from about 200 Da to about 5,000,000 Da, and more preferably the molecular weight ranges from about 2,000 Da to about 1,000,000 Da.

For example, a personal care product of this invention, comprises the polymer-bound UV-B absorber methyl-2-aminobenzoate. Its reaction with poly(methyl vinyl ether-co-maleic anhydride) can be represented as:

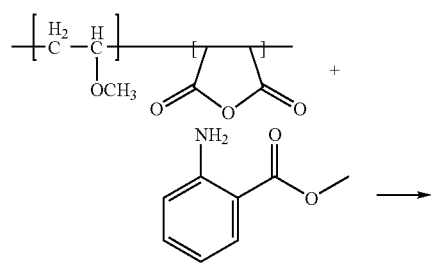

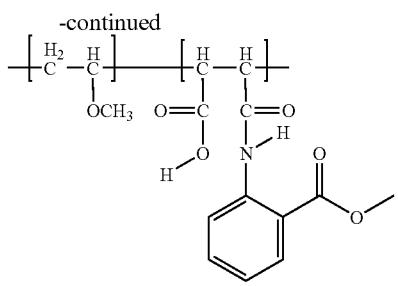

The amic acid form, as shown, can be converted from its amic acid to cyclic imide form by heating, using a catalyst, or a combination of both:

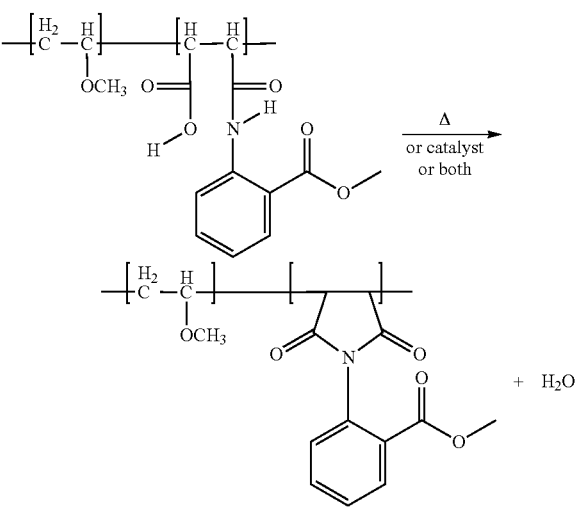

As a second example, a UV-A absorber, 2-aminobenzophenone, and a UV-B absorber, amino-2-benzoate, can be reacted onto poly(methyl vinyl ether-co-maleic anhydride) to provide a single polymeric molecule with broad UV spectrum absorption functionality:

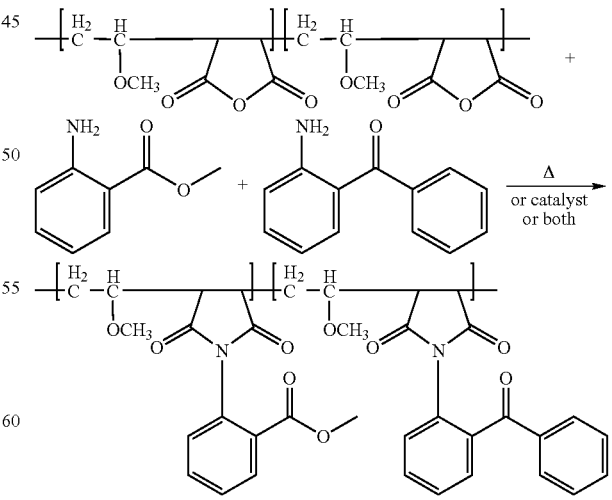

In the above reaction scheme it is understood that at least one 2-aminobenzophenone molecule has been grafted onto at least one of the maleic anhydride groups of the starting polymer, and at least one methyl-2-aminobenzoate molecular has been grafted onto at least one of the maleic anhydride groups, which may be adjacent or not adjacent to the first maleic anhydride group. In the finished product only the imide forms are shown, as the immediate amic acid forms are not illustrated.

For solution reactions, temperatures are conveniently controlled by judicious choice of solvents within an appropriate boiling range. Temperatures in this case range from 20° C. to about 225° C., preferably from 75° C. to 200° C., and most preferably from 80° C. to 200° C. Reaction times for solvent reaction range from several minutes to 48 hours. Higher reaction temperatures will reduce time for conversion to the desired product(s). Preferably, solvent reaction times will be between 15 minutes and 8 hours and most preferably between 15 minutes and 4 hours. In addition, azeotropic water removal from the solvent will facilitate most solvent reactions.

The use of certain reactants and selection of reaction temperature may result in a reacting system of high viscosity, which may reduce the reaction yield. A resolution to this problem is the addition of an optional reaction solvent. The reaction comprising the UV absorber and the graft host may be carried out without or with added inert solvents, including: benzene, toluene, xylene, mesitylene, chlorobenzene, dimethylformamide, tetrahydrofuran, aliphatic hydrocarbons, and the Ceraphyl® emollients product line of International Specialty Products (Wayne, N.J.), such as diisopropyl adipate (Ceraphyl® 230).

Since the UV absorber actives are covalently bonded to the anhydride-comprising polymer, they are not lost from the reacted product by volatilization, migration, or other mechanisms even at high temperatures. As a result, the compositions of this invention are particularly useful for extended product service life.

Optional: Initiator

An optional free radical initiator may be added to the reactants to graft the cited UV absorber onto the graft host. Advantages of using an optional initiator(s) may include lower reaction temperatures and/or more complete extent of reaction.

Compounds capable of initiating the free-radical polymerization include those materials known to function in the prescribed manner, and include the peroxo and azo classes of materials. Exemplary peroxo and azo compounds include, but are not limited to: acetyl peroxide; azo bis-(2-amidinopropane)dihydrochloride; azo bis-isobutyronitrile; 2,2'-azo bis-(2-methylbutyronitrile); benzoyl peroxide; di-tert-amyl peroxide; di-tert-butyl diperphthalate; butyl peroctoate; tert-butyl dicumyl peroxide; tert-butyl hydroperoxide; tert-butyl perbenzoate; tert-butyl permaleate; tert-butyl perisobutylrate; tert-butyl peracetate; tert-butyl perpivalate; para-chlorobenzoyl peroxide; cumene hydroperoxide; diacetyl peroxide; dibenzoyl peroxide; dicumyl peroxide; didecanoyl peroxide; dilauroyl peroxide; diisopropyl peroxodicarbamate; dioctanoyl peroxide; lauroyl peroxide; octanoyl peroxide; succinyl peroxide; and bis-(ortho-toluoyl) peroxide.

Also suitable to initiate the free-radical polymerization are initiator mixtures or redox initiator systems, including: ascorbic acid/iron(II) sulfate/sodium peroxodisulfate, tert-butyl hydroperoxide/sodium disulfite, and tert-butyl hydroperoxide/sodium hydroxymethanesulfinate.

Optional Polymerizable Units

The polymers in the above description must contain at least one anhydride group, preferably maleic anhydride or one of its derivatives, in order to facilitate the reaction with the select UV absorber(s). In addition, the polymers by any of the three methods may non-homopolymers, containing optional polymerizable units. Some of these units were introduced earlier in the description of polymers having an anhydride unit as part of the backbone, such as styrene and methyl vinyl ether. However, compositions of the invention are not limited to these; in fact, the choice of other polymerizable units extends functionality into the chosen application arts compositions.

These optional polymerizable unit(s) may be selected from the group consisting of: alkylacrylamides including acrylamide and methacrylamide, acrylates, allyl derivatives, benzoxanes, cinnamyls, epoxides, fumarates, maleates, maleimides, oxazolines, oxetanes, styrenes, vinyl acetates, vinyl acrylamides, vinyl carbonates, vinyl ethers, vinyl imidazoles, vinyl triazoles, vinyl lactams, vinyl pyridines, vinyl silanes, vinyl sulfones, and mixtures thereof. As before, polymers comprising these optional polymerizable units may be a random, blocked, or alternating polymers.

Additional Formulation Ingredients and Adjuvants

It is anticipated that the compositions of the invention will contain formulation ingredients and/or adjuvants in addition to the polymer-bound UV-absorber(s). Such ingredients further enhance the properties of the finished product and may be incorporated without altering the scope of the current invention, and may be included in order to produce the necessary formulated personal care products.

For example, the personal care composition of the invention also can contain one or more additional cosmetically acceptable additives chosen from conditioning agents, protecting agents, such as, for example, hydrosoluble, antiradical agents, antioxidants, vitamins and pro-vitamins, fixing agents, oxidizing agents, reducing agents, dyes, cleansing agents, anionic, cationic, nonionic and amphoteric surfactants, thickeners, perfumes, pearlizing agents, stabilizers, pH adjusters, filters, preservatives, hydroxy acids, cationic and nonionic polyether associative polyurethanes, polymers other than the cationic polymer described herein, vegetable oils, mineral oils, synthetic oils, polyols such as glycols and glycerol, silicones, aliphatic alcohols, colorants, bleaching agents, highlighting agents and sequestrants. These additives are present in the composition according to the invention in proportions that may range from 0% to 20% by weight in relation to the total weight of the composition. The precise amount of each additive may be easily determined by an expert in the field according to its nature and its function.

Any known conditioning agent is useful in the personal care compositions of this invention. Conditioning agents function to improve the cosmetic properties of the hair, particularly softness, thickening, untangling, feel, and static electricity and may be in liquid, semi-solid, or solid form such as oils, waxes, or gums. Similarly, any known skin altering agent is useful in the compositions of this invention. Preferred conditioning agents include cationic polymers, cationic surfactants and cationic silicones.

Conditioning agents may be chosen from synthesis oils, mineral oils, vegetable oils, fluorinated or perfluorinated oils, natural or synthetic waxes, silicones, cationic polymers, proteins and hydrolyzed proteins, ceramide type compounds, cationic surfactants, fatty amines, fatty acids and their derivatives, as well as mixtures of these different compounds.

The synthesis oils include polyolefins, e.g., poly-α-olefins such as polybutenes, polyisobutenes and polydecenes. The polyolefins can be hydrogenated.

The mineral oils suitable for use in the compositions of the invention include hexadecane and oil of paraffin.

A list of suitable animal and vegetable oils comprises sunflower, corn, soy, avocado, jojoba, squash, raisin seed, sesame seed, walnut oils, fish oils, glycerol tricaprocaprylate, Purcellin oil or liquid jojoba, and blends thereof.

Suitable natural or synthetic oils include eucalyptus, lavender, vetiver, litsea cubeba, lemon, sandalwood, rosemary, chamomile, savory, nutmeg, cinnamon, hyssop, caraway, orange, geranium, cade, and bergamot.

Suitable natural and synthetic waxes include carnauba wax, candelila wax, alfa wax, paraffin wax, ozokerite wax, vegetable waxes such as olive wax, rice wax, hydrogenated jojoba wax, absolute flower waxes such as black currant flower wax, animal waxes such as bees wax, modified bees wax (cerabellina), marine waxes and polyolefin waxes such as polyethylene wax, and blends thereof.

The cationic polymers that may be used as a conditioning agent according to the invention are those known to improve the cosmetic properties of hair treated by detergent compositions. The expression "cationic polymer" as used herein, indicates any polymer containing cationic groups and/or ionizable groups in cationic groups. The cationic polymers used generally have a molecular weight the average number of which falls between about 500 Da and 5,000,000 Da and preferably between 1000 Da and 3,000,000 Da.

The preferred cationic polymers are chosen from among those containing units including primary, secondary, tertiary, and/or quaternary amine groups that may either form part of the main polymer chain or a side chain.

Useful cationic polymers include known polyamine, polyaminoamide, and quaternary polyammonium types of polymers, such as:

(1) homopolymers and copolymers derived from acrylic or methacrylic esters or amides. The copolymers can contain one or more units derived from acrylamides, methacrylamides, diacetone acrylamides, acrylamides and methacrylamides, acrylic or methacrylic acids or their esters, vinyllactams such as vinyl pyrrolidone or vinyl caprolactam, and vinyl esters. Specific examples include: copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone/dialkylaminoalkyl acrylate or methacrylate, optionally quaternized, such as the products sold under the name Gafquat® by International Specialty Products; the dimethyl amino ethyl methacrylate/vinyl caprolactam/vinyl pyrrolidone terpolymers, such as the product sold under the name Gaffix® VC 713 by International Specialty Products; the vinyl pyrrolidone/methacrylamidopropyl dimethylamine copolymer, marketed under the name Styleze® CC 10 by International Specialty Products; and the vinyl pyrrolidone/quaternized dimethyl amino propyl methacrylamide copolymers such as the product sold under the name Gafquat® HS 100 by International Specialty Products (Wayne, N.J.).

(2) derivatives of cellulose ethers containing quaternary ammonium groups, such as hydroxy ethyl cellulose quaternary ammonium that has reacted with an epoxide substituted by a trimethyl ammonium group.

(3) derivatives of cationic cellulose such as cellulose copolymers or derivatives of cellulose grafted with a hydrosoluble quaternary ammonium monomer, as described in U.S. Pat. No. 4,131,576, such as the hydroxy alkyl cellulose, and the hydroxymethyl-, hydroxyethyl- or hydroxypropyl-cellulose grafted with a salt of methacryloyl ethyl trimethyl ammonium, methacrylamidopropyl trimethyl ammonium, or dimethyl diallyl ammonium.

(4) cationic polysaccharides such as described in U.S. Pat. Nos. 3,589,578 and 4,031,307, guar gums containing cationic trialkyl ammonium groups and guar gums modified by a salt, e.g., chloride of 2,3-epoxy propyl trimethyl ammonium.

(5) polymers composed of piperazinyl units and alkylene or hydroxy alkylene divalent radicals with straight or branched chains, possibly interrupted by atoms of oxygen, sulfur, nitrogen, or by aromatic or heterocyclic cycles, as well as the products of the oxidation and/or quaternization of such polymers.

(6) water-soluble polyamino amides prepared by polycondensation of an acid compound with a polyamine. These polyamino amides may be reticulated.

(7) derivatives of polyamino amides resulting from the condensation of polyalcoylene polyamines with polycarboxylic acids followed by alcoylation by bi-functional agents.

(8) polymers obtained by reaction of a polyalkylene polyamine containing two primary amine groups and at least one secondary amine group with a dioxycarboxylic acid chosen from among diglycolic acid and saturated dicarboxylic aliphatic acids having 3 to 8 atoms of carbon. Such polymers are described in U.S. Pat. Nos. 3,227,615 and 2,961,347.

(9) the cyclopolymers of alkyl dialyl amine or dialkyl diallyl ammonium such as the homopolymer of dimethyl diallyl ammonium chloride and copolymers of diallyl dimethyl ammonium chloride and acrylamide.

(10) quaternary diammonium polymers such as hexadimethrine chloride.

(11) quaternary polyammonium polymers, including, for example, Mirapol® A 15, Mirapol® AD1, Mirapol® AZ1, and Mirapol® 175 products sold by Miranol.

(12) the quaternary polymers of vinyl pyrrolidone and vinyl imidazole such as the products sold under the names Luviquat® FC 905, FC 550, and FC 370 by BASF Corp. (Ludwigshafen, Del.).

(13) quaternary polyamines.

(14) reticulated polymers known in the art.

Other cationic polymers that may be used within the context of the invention are cationic proteins or hydrolyzed cationic proteins, polyalkyleneimines such as polyethyleneimines, polymers containing vinyl pyridine or vinyl pyridinium units, condensates of polyamines and epichlorhydrins, quaternary polyurethanes, and derivatives of chitin.

Preferred cationic polymers are derivatives of quaternary cellulose ethers, the homopolymers and copolymers of dimethyl diallyl ammonium chloride, quaternary polymers of vinyl pyrrolidone and vinyl imidazole, and mixtures thereof.

The conditioning agent can be any silicone known by those skilled in the art to be useful as a conditioning agent. The silicones suitable for use according to the invention include polyorganosiloxanes that are insoluble in the composition. The silicones may be present in the form of oils, waxes, resins, or gums. They may be volatile or non-volatile. The silicones can be selected from polyalkyl siloxanes, polyaryl siloxanes, polyalkyl aryl siloxanes, silicone gums and resins, and polyorgano siloxanes modified by organofunctional groups, and mixtures thereof.

Suitable polyalkyl siloxanes include polydimethyl siloxanes with terminal trimethyl silyl groups or terminal dimethyl silanol groups (dimethiconol) and polyalkyl ($C_1$-$C_{20}$) siloxanes.

Suitable polyalkyl aryl siloxanes include polydimethyl methyl phenyl siloxanes and polydimethyl diphenyl siloxanes, linear or branched.

The silicone gums suitable for use herein include polydiorganosiloxanes preferably having a number-average molecular weight between 200,000 Da and 1,000,000, Da used alone or mixed with a solvent. Examples include polymethyl siloxane, polydimethyl siloxane/methyl vinyl siloxane gums, polydimethyl siloxane/diphenyl siloxane, polydimethyl siloxane/phenyl methyl siloxane and polydimethyl siloxane/diphenyl siloxane/methyl vinyl siloxane.

Suitable silicone resins include silicones with a dimethyl/trimethyl siloxane structure and resins of the trimethyl siloxysilicate type.

The organo-modified silicones suitable for use in the invention include silicones such as those previously defined and containing one or more organofunctional groups attached by means of a hydrocarbon radical and grafted siliconated polymers. Particularly preferred are amino functional silicones.

The silicones may be used in the form of emulsions, nano-emulsions, or micro-emulsions.

The conditioning agent can be a protein or hydrolyzed cationic or non-cationic protein. Examples of these compounds include hydrolyzed collagens having triethyl ammonium groups, hydrolyzed collagens having trimethyl ammonium and trimethyl stearyl ammonium chloride groups, hydrolyzed animal proteins having trimethyl benzyl ammonium groups (benzyltrimonium hydrolyzed animal protein), hydrolyzed proteins having groups of quaternary ammonium on the polypeptide chain, including at least one $C_1$-$C_{18}$ alkyl.

Hydrolyzed proteins include Croquat L, in which the quaternary ammonium groups include a $C_{12}$ alkyl group, Croquat M, in which the quaternary ammonium groups include $C_{10}$-$C_{18}$ alkyl groups, Croquat S in which the quaternary ammonium groups include a $C_{18}$ alkyl group and Crotein Q in which the quaternary ammonium groups include at least one $C_1$-$C_{18}$ alkyl group. These products are sold by Croda.

The conditioning agent can comprise quaternized vegetable proteins such as wheat, corn, or soy proteins such as cocodimonium hydrolyzed wheat protein, laurdimonium hydrolyzed wheat protein and steardimonium hydrolyzed wheat protein, 2-N-stearoyl amino-octadecane-1,3-diol, 2-N-behenoyl amino-octadecane-1,3-diol, 2-N-[2-hydroxy-palmitoyl]-amino-octadecane-1,3-diol, 2-N-stearoyl amino-octadecane-1,3,4-triol, N-stearoyl phytosphingosine, 2-N-palmitoyl amino-hexadecane-1,3-diol, bis-(N-hydroxy ethyl N-cetyl) malonamide, N-(2-hydroxy ethyl)-N-(3-cetoxyl-2-hydroxy propyl) amide of cetylic acid, N-docosanoyl N-methyl-D-glucamine and mixtures of such compounds.

The conditioning agent can be a cationic surfactant such as a salt of a primary, secondary, or tertiary fatty amine, optionally polyoxyalkylenated, a quaternary ammonium salt, a derivative of imadazoline, or an amine oxide. Suitable examples include mono-, di-, or tri-alkyl quaternary ammonium compounds with a counterion such as a chloride, methosulfate, tosylate, etc. including, but not limited to, cetrimonium chloride, dicetyldimonium chloride, behentrimonium methosulfate, and the like. The presence of a quaternary ammonium compound in conjunction with the polymer described above reduces static and enhances combing of hair in the dry state. The polymer also enhances the deposition of the quaternary ammonium compound onto the hair substrate thus enhancing the conditioning effect of hair.

The conditioning agent can be any fatty amine known to be useful as a conditioning agent; e.g. dodecyl, cetyl or stearyl amines, such as stearamidopropyl dimethylamine.

The conditioning agent can be a fatty acid or derivatives thereof known to be useful as conditioning agents. Suitable fatty acids include myristic acid, palmitic acid, stearic acid, behenic acid, oleic acid, linoleic acid, and isostearic acid. The derivatives of fatty acids include carboxylic ester acids including mono-, di-, tri- and tetra-carboxylic acids.

The conditioning agent can be a fluorinated or perfluorinated oil. The fluoridated oils may also be fluorocarbons such as fluoramines, e.g., perfluorotributylamine, fluoridated hydrocarbons, such as perfluorodecahydronaphthalene, fluoroesters, and fluoroethers.

Of course, mixtures of two or more conditioning agents can be used.

The conditioning agent or agents can be present in an amount of 0.001% to 20%, preferably from 0.01% to 10%, and even more preferably from 0.1% to 3% by weight based on the total weight of the final composition.

The composition of the invention can contain one or more protecting agents to prevent or limit the degrading effects of natural physical and/or chemical assaults on the keratinous materials.

The antioxidants or antiradical agents can be selected from phenols such as BHA (tert-butyl-4-hydroxy anisole), BHT (2,6-di-tert-butyl-p-cresol), TBHQ (tert-butyl hydroquinone), polyphenols such as proanthocyanodic oligomers, flavonoids, hindered amines such as tetra amino piperidine, erythorbic acid, polyamines such as spermine, cysteine, glutathione, superoxide dismutase, and lactoferrin.

The vitamins can be selected from ascorbic acid (vitamin C), vitamin E, vitamin E acetate, vitamin E phosphate, B vitamins such as B3 and B5, vitamin PP (i.e., niacin), vitamin A, and derivatives thereof. The provitamins can be selected from panthenol and retinol.

The protecting agent can be present in an amount 0.001% to 20% by weight, preferably from 0.01% to 10% by weight, and more preferably 0.1 to 5% by weight of the total weight of the final composition.

In addition, the compositions according to the invention advantageously include at least one surfactant, which can be present in an amount of 0.1% and 60% preferably 1% and 40%, and more preferably 5% and 30% by weight based on the total weight of the composition. The surfactant may be chosen from among anionic, amphoteric, or non-ionic surfactants, or mixtures of them known to be useful in personal care compositions.

Additional thickeners or viscosity increasing agents may be included in the composition of the invention, such as: Acetamide MEA; acrylamide/ethalkonium chloride acrylate copolymer; acrylamide/ethyltrimonium chloride acrylate/ethalkonium chloride acrylate copolymer; acrylamides copolymer; acrylamide/sodium acrylate copolymer; acrylamide/sodium acryloyldimethyltaurate copolymer; acrylates/acetoacetoxyethyl methacrylate copolymer; acrylates/beheneth-25 methacrylate copolymer; acrylates/$C_{10}$-$C_{30}$ alkyl acrylate crosspolymer; acrylates/ceteth-20 itaconate copolymer; acrylates/ceteth-20 methacrylate copolymer; acrylates/laureth-25 methacrylate copolymer; acrylates/palmeth-25 acrylate copolymer; acrylates/palmeth-25 itaconate copolymer; acrylates/steareth-50 acrylate copolymer; acrylates/steareth-20 itaconate copolymer; acrylates/steareth-20 methacrylate copolymer; acrylates/stearyl methacrylate copolymer; acrylates/vinyl isodecanoate crosspolymer; acrylic acid/acrylonitrogens copolymer; adipic acid/methyl DEA crosspolymer; agar; agarose; alcaligenes polysaccharides; algin; alginic acid; almondamide DEA; almondamidopropyl betaine; aluminum/magnesium hydroxide stearate; ammonium acrylates/acrylonitrogens copolymer; ammonium acrylates copolymer; ammonium acryloyldimethyltaurate/vinyl formamide copolymer; ammonium acryloyldimethyltaurate/VP copolymer; ammonium alginate; ammonium chloride; ammonium polyacryloyldimethyl taurate; ammonium sulfate; amylopectin; apricotamide DEA; apricotamidopropyl betaine; arachidyl alcohol; arachidyl glycol; arachis hypogaea (peanut) flour; ascorbyl methylsilanol pectinate; astragalus gummifer gum; attapulgite; avena sativa (oat) kernel flour; avocadamide DEA; avocadamidopropyl betaine; azelamide MEA; babassuamide DEA; babassuamide MEA; babassuamidopropyl betaine; behenamide DEA; behenamide MEA; behenamidopropyl betaine; behenyl betaine; bentonite; butoxy chitosan; caesalpinia spinosa gum; calcium alginate; calcium carboxymethyl cellulose; calcium carrageenan; calcium chloride; calcium potassium carbomer; calcium starch octenylsuccinate; C20-40 alkyl stearate; canolamidopropyl betaine; capramide DEA; capryl/capramidopropyl betaine; carbomer; carboxybutyl chitosan; carboxymethyl cellulose acetate butyrate; carboxymethyl chitin; carboxymethyl chitosan; carboxymethyl dextran; carboxymethyl hydroxyethylcellulose; carboxymethyl hydroxypropyl guar; carnitine; cellulose acetate propionate carboxylate; cellulose gum; ceratonia siliqua gum; cetearyl alcohol; cetyl alcohol; cetyl babassuate; cetyl betaine; cetyl glycol; cetyl hydroxyethylcellulose; chimyl alcohol; cholesterol/HDI/pullulan copolymer; cholesteryl hexyl dicarbamate pullulan; citrus aurantium dulcis (orange) peel extract; cocamide DEA; cocamide MEA; cocamide MIPA; cocamidoethyl betaine; cocamidopropyl betaine; cocamidopropyl hydroxysultaine; coco-betaine; coco-hydroxysultaine; coconut alcohol; coco/oleamidopropyl betaine; coco-Sultaine; cocoyl sarcosinamide DEA; cornamide/cocamide DEA; comamide DEA; croscarmellose; crosslinked bacillus/glucose/sodium glutamate ferment; cyamopsis tetragonoloba (guar) gum; decyl alcohol; decyl betaine; dehydroxanthan gum; dextrin; dibenzylidene sorbitol; diethanolaminooleamide DEA; diglycol/CHDM/isophthalates/SIP copolymer; dihydroabietyl behenate; dihydrogenated tallow benzylmonium hectorite; dihydroxyaluminum aminoacetate; dimethicone/PEG-10 crosspolymer; dimethicone/PEG-15 crosspolymer; dimethicone propyl PG-betaine; dimethylacrylamide/acrylic acid/polystyrene ethyl methacrylate copolymer; dimethylacrylamide/sodium acryloyldimethyltaurate crosspolymer; disteareth-100 IPDI; DMAPA acrylates/acrylic acid/acrylonitrogens copolymer; erucamidopropyl hydroxysultaine; ethylene/sodium acrylate copolymer; gelatin; gellan gum; glyceryl alginate; glycine soja (soybean) flour; guar hydroxypropyltrimonium chloride; hectorite; hyaluronic acid; hydrated silica; hydrogenated potato starch; hydrogenated tallow; hydrogenated tallowamide DEA; hydrogenated tallow betaine; hydroxybutyl methylcellulose; hydroxyethyl acrylate/sodium acryloyldimethyl taurate copolymer; hydroxyethylcellulose; hydroxyethyl chitosan; hydroxyethyl ethylcellulose; hydroxyethyl stearamide-MIPA; hydroxylauryl/hydroxymyristyl betaine; hydroxypropylcellulose; hydroxypropyl chitosan; hydroxypropyl ethylenediamine carbomer; hydroxypropyl guar; hydroxypropyl methylcellulose; hydroxypropyl methylcellulose stearoxy ether; hydroxypropyl starch; hydroxypropyl starch phosphate; hydroxypropyl xanthan gum; hydroxystearamide MEA; isobutylene/sodium maleate copolymer; isostearamide DEA; isostearamide MEA; isostearamide mIPA; isostearamidopropyl betaine; lactamide MEA; lanolinamide DEA; lauramide DEA; lauramide MEA; lauramide MIPA; lauramide/myristamide DEA; lauramidopropyl betaine; lauramidopropyl hydroxysultaine; laurimino bispropanediol; lauryl alcohol; lauryl betaine; lauryl hydroxysultaine; lauryl/myristyl glycol hydroxypropyl ether; lauryl sultaine; lecithinamide DEA; linoleamide DEA; linoleamide MEA; linoleamide MIPA; lithium magnesium silicate; lithium magnesium sodium silicate; macrocystis pyrifera (kelp); magnesium alginate; magnesium/aluminum/hydroxide/carbonate; magnesium aluminum silicate; magnesium silicate; magnesium trisilicate; methoxy PEG-22/dodecyl glycol copolymer; methylcellulose; methyl ethylcellulose; methyl hydroxyethylcellulose; microcrystalline cellulose; milkamidopropyl betaine; minkamide DEA; minkamidopropyl betaine; MIPA-myristate; montmorillonite; Moroccan lava clay; myristamide DEA; myristamide MEA; myristamide MIPA; myristamidopropyl betaine; myristamidopropyl hydroxysultaine; myristyl alcohol; myristyl betaine; natto gum; nonoxynyl hydroxyethylcellulose; oatamide MEA; oatamidopropyl betaine; octacosanyl glycol isostearate; octadecene/MA copolymer; oleamide DEA; oleamide MEA; oleamide MIPA; oleamidopropyl betaine; oleamidopropyl hydroxysultaine; oleyl betaine; olivamide DEA; olivamidopropyl betaine; oliveamide MEA; palmamide DEA; palmamide MEA; palmamide MIPA; palmamidopropyl betaine; palmitamide DEA; palmitamide MEA; palmitamidopropyl betaine; palm kernel alcohol; palm kernelamide DEA; palm kernelamide MEA; palm kernelamide MIPA; palm kernelamidopropyl betaine; peanutamide MEA; peanutamide MIPA; pectin; PEG-800; PEG-crosspolymer; PEG-150/decyl alcohol/SMDI copolymer; PEG-175 diisostearate; PEG-190 distearate; PEG-15 glyceryl tristearate; PEG-140 glyceryl tristearate; PEG-240/HDI copolymer bis-decyltetradeceth-20 ether; PEG-100/IPDI copolymer; PEG-180/laureth-50/TMMG copolymer; PEG-10/lauryl dimethicone crosspolymer; PEG-15/lauryl dimethicone crosspolymer; PEG-2M; PEG-5M; PEG-7M; PEG-9M; PEG-14M; PEG-20M; PEG-23M; PEG-25M; PEG-45M; PEG-65M; PEG-90M; PEG-115M; PEG-160M; PEG-180M; PEG-120 methyl glucose trioleate; PEG-180/octoxynol-40/TMMG copolymer; PEG-150 pentaerythrityl tetrastearate; PEG-4 rapeseedamide; PEG-150/stearyl alcohol/SMDI copolymer; phaseolus angularis seed powder; polianthes tuberosa extract; polyacrylate-3; polyacrylic acid; polycyclopentadiene; polyether-1; polyethylene/isopropyl maleate/MA copolyol; polyglyceryl-3 disiloxane dimethicone; polyglyceryl-3 polydimethylsiloxyethyl dimethicone; polymethacrylic acid; polyquaternium-52; polyvinyl alcohol; potassium alginate; potassium aluminum polyacrylate; potassium carbomer; potassium carrageenan; potassium chloride; potassium palmate; potassium polyacrylate; potassium sulfate; potato starch modified; PPG-2 cocamide; PPG-1 hydroxyethyl caprylamide; PPG-2 hydroxyethyl cocamide; PPG-2 hydroxyethyl coco/isostearamide; PPG-3 hydroxyethyl soyamide; PPG-14 laureth-60 hexyl dicarbamate; PPG-14 laureth-60 isophoryl dicarbamate; PPG-14 palmeth-60 hexyl dicarbamate; propylene glycol alginate; PVP/decene copolymer; PVP montmorillonite; pyrus cyclonia seed; pyrus malus (apple) fiber; rhizobian gum; ricebranamide DEA; ricinoleamide DEA; ricinoleamide MEA; ricinoleamide MIPA; ricinoleamidopropyl betaine; ricinoleic acid/adipic acid/AEEA copolymer; rosa multiflora flower wax; sclerotium gum; sesamide DEA; sesamidopropyl betaine; sodium acrylate/acryloyldimethyl taurate copolymer; sodium acrylates/acrolein copolymer; sodium acrylates/acrylonitrogens copolymer; sodium acrylates copolymer; sodium acrylates crosspolymer; sodium acrylate/sodium acrylamidomethylpropane sulfonate copolymer; sodium acrylates/vinyl isodecanoate crosspolymer; sodium acrylate/vinyl alcohol copolymer; sodium carbomer; sodium carboxymethyl chitin; sodium carboxymethyl dextran; sodium carboxymethyl beta-glucan; sodium carboxymethyl starch; sodium carrageenan; sodium cellulose sulfate; sodium chloride; sodium cyclodextrin sulfate; sodium hydroxypropyl starch phosphate; sodium isooctylene/MA copolymer; sodium magnesium fluorosilicate; sodium oleate; sodium palmitate; sodium palm kernelate; sodium polyacrylate; sodium polyacrylate starch; sodium polyacryloyldimethyl taurate; sodium polygamma-glutamate; sodium polymethacrylate; sodium polystyrene sulfonate; sodium silicoaluminate; sodium starch octenylsuccinate; sodium stearate; sodium stearoxy PG-hydroxyethylcellulose sulfonate; sodium styrene/acrylates copolymer; sodium sulfate; sodium tallowate; sodium tauride acrylates/acrylic acidlacrylonitrogens copolymer; sodium tocopheryl phosphate; solanum tuberosum (potato) starch; soyamide DEA; soyamidopropyl betaine; starch/acrylates/acrylamide copolymer; starch hydroxypropyltrimonium chloride; stearamide AMP; stearamide DEA; stearamide DEA-distearate; stearamide DIBA-stearate; stearamide MEA; stearamide MEA-stearate; stearamide MIPA; stearamidopropyl betaine; steareth-60 cetyl ether; steareth-100/PEG-136/HDI copolymer; stearyl alcohol; stearyl betaine; sterculia urens gum; synthetic fluorphlogopite; tallamide DEA; tallow alcohol; tallowamide DEA; tallowamide MEA; tallowamidopropyl betaine; tallowamidopropyl hydroxysultaine; tallowamine oxide; tallow betaine; tallow dihydroxyethyl betaine; tamarindus indica seed gum; tapioca starch; TEA-alginate; TEA-carbomer; TEA-hydrochloride; trideceth-2 carboxamide MEA; tridecyl alcohol; triethylene glycol dibenzoate; trimethyl pentanol hydroxyethyl ether; triticum vulgare (wheat) germ powder; triticum vulgare (wheat) kernel flour; triticum vulgare (wheat) starch; tromethamine acrylates/acrylonitrogens copolymer; tromethamine magnesium aluminum silicate; undecyl alcohol; undecylenamide DEA; undecylenamide MEA; undecylenamidopropyl betaine; welan gum; wheat germamide DEA; wheat germamidopropyl betaine; xanthan gum; yeast beta-glucan; yeast polysaccharides and zea mays (corn) starch.

Preferred thickeners or viscosity increasing agents include carbomer, aculyn and Stabileze®, e.g. crosslinked acrylic acid, crosslinked poly(methylvinyl ether/maleic anhydride) copolymer, acrylamides, carboxymethyl cellulose and the like.

The compositions according to the invention may be used to wash and treat keratinous material such as hair, skin, eyelashes, eyebrows, fingernails, lips, and hairy skin.

The compositions according to the invention may also take the form of after-shampoo compositions, to be rinsed off or not, for permanents, straightening, waving, dyeing, or bleaching, or the form of rinse compositions to be applied before or after dyeing, bleaching, permanents, straightening, relaxing, waving or even between the two stages of a permanent or straightening process.

The compositions of the invention may also take the form of skin-washing compositions, and particularly in the form of solutions or gels for the bath or shower, or of make-up removal products.

The compositions of the invention may also be in the form of aqueous or hydro-alcoholic solutions for skin and/or hair care.

The compositions according to the invention can be detergent compositions such as shampoos, bath gels, and bubble baths. In this mode, the compositions will comprise a generally aqueous washing base. The surfactant or surfactants that form the washing base may be chosen alone or in blends, from known anionic, amphoteric, or non-ionic surfactants. The quantity and quality of the washing base must be sufficient to impart a satisfactory foaming and/or detergent value to the final composition. The washing base can be from 4% to 50% by weight, preferably from 6% to 35% by weight, and even more preferentially from 8% to 25% by weight of the total weight of the final composition.

With respect to personal care products, additional formulation ingredients of particular interest are those selected from the list comprising: anti-oxidants, bronzing/self-tanning agents, colorants, defoamers, emollients, fragrances, humectants, insect repellants, lower monoalcohols, lower polyols, micro- and nano-particulate UV absorbants, moisturizers, pigments, preservatives, propellants, oils, surfactants, thickeners, water, and waxes.

With respect to coatings, packaging, plastics, and/or printing product, additional formulation ingredients of particular interest are selected from the list comprising: colorants, defoamers, dyes, fragrances, lacquers, lakes, latexes, micro- and nano-particulate UV absorbents, pigments, plasticizers, preservatives (including biocides), solvents, surfactants, thickeners, varnishes, and water.

Product Forms

The personal care compositions comprising the described polymer-bound UV absorber find use in a large number of product forms. In one embodiment, the UV absorber composition takes the form of a film, e.g., applied neat or from a solvent-evaporation step. In preferred embodiments, the compositions are employed in sun-care formulations.

Cosmetic compositions according to the invention may, for example, be used as care and/or sun protection product for the face and/or the body having a consistency ranging from liquid to semiliquid (e.g., milks, creams), and gels, creams, pastes, powders (including compacted powders), and wax-like compositions (e.g., lip balms).

Due to the great potential for controlling the anhydride and UV absorber addition levels, the product may comprise from about 0.01% to about 100% of the described UV absorber composition.

For compositions intended to protect the hair from UV radiation, suitable product forms include, but not limited to: conditioners, dispersions, emulsions, gels, lotions, mists, mousses, shampoos, and sprays.

Optionally, formulations comprising the UV absorber composition may be packaged as an aerosol and may be provided in the form of a mousse or a spray. It may be advantageous to utilize known propellants (e.g., hydrofluorinated compounds dichlorodifluoromethane, difluoroethane, dimethyl ether, isobutene, N-butane, propane, trichlorofluoromethane) to aide in their delivery.

In a different embodiment, compositions of this invention may be provided in the form of vaporizable fluid lotions to be applied to the skin or the hair. Pressurized devices are a suitable means for vaporizing fluid lotions, and are known to one skilled in the art. For example, they are described in U.S. Pat. Nos. 4,077,441 and 4,850,517.

Characterizing of the Polymer-Bound UV Absorber

The UV absorber reaction product can be analyzed by known techniques to characterize the product. Especially preferred are the techniques of $^{13}C$ nuclear magnetic resonance (NMR) spectroscopy, gas chromatography (GC), and gel permeation chromatography (GPC) in order to decipher polymer identity, residual UV absorber concentrations, polymer molecular weight, and polymer molecular weight distribution.

Nuclear magnetic resonance (NMR) spectroscopy is an especially preferred method to probe the polymerization product in terms of chemical properties such as monomeric composition, sequencing and tacticity. Analytical equipment suitable for these analyses include the Inova 400-MR NMR System by Varian Inc. (Palo Alto, Calif.). References broadly describing NMR include: Yoder, C. H. and Schaeffer Jr., C. D., *Introduction to Multinuclear NMR*, The Benjamin/Cummings Publishing Company, Inc., 1987; and Silverstein, R. M., et al., *Spectrometric Identification of Organic Compounds*, John Wiley & Sons, 1981, which are incorporated in their entirety by reference.

Residual monomer levels can be measured by GC, which can be used to indicate the extent of reactant conversion by the polymerization process. GC analytical equipment to perform these tests are commercially available, and include the following units: Series 5880, 5890, and 6890 GC-FID and GC-TCD by Agilent Technologies, Inc. (Santa Clara, Calif.). GC principles are described in *Modern Practice of Gas Chromatography*, third edition (John Wiley & Sons, 1995) by Robert L. Grob and Eugene F. Barry, which is hereby incorporated in its entirety by reference.

GPC is an analytical method that separates molecules based on their hydrodynamic volume (or size) in solution of the mobile phase, such as hydroalcoholic solutions with surfactants. GPC is a preferred method for measuring polymer molecular weight distributions. This technique can be performed on known analytical equipment sold for this purpose, and include the TDAmax™ Elevated Temperature GPC System and the RImax™ Conventional Calibration System by Viscotek™ Corp. (Houston, Tex.). In addition, GPC employs analytical standards as a reference, of which a plurality of narrow-distribution polyethylene glycol and polyethylene oxide standards representing a wide range in molecular weight is the preferred. These analytical standards are available for purchase from Rohm & Haas Company (Philadelphia, Pa.) and Varian Inc. (Palo Alto, Calif.). GPC is described in the following texts, which are hereby incorporated in their entirety by reference: Schroder, E., et al., *Polymer Characterization*, Hanser Publishers, 1989; Billingham, N.C., *Molar Mass Measurements in Polymer Science*, Halsted Press, 1979; and Billmeyer, F., *Textbook of Polymer Science*, Wiley Interscience, 1984.

The invention will now be described with reference to the following examples:

EXAMPLES

Polymer-Bound UV Absorber 1

Grafting UV-B Absorber onto poly(methyl vinyl ether-co-maleic anhydride) polymer

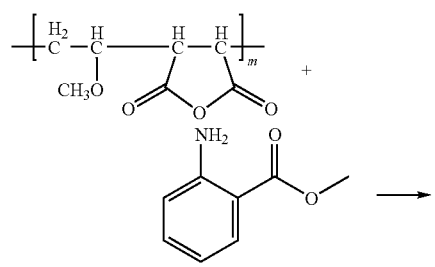

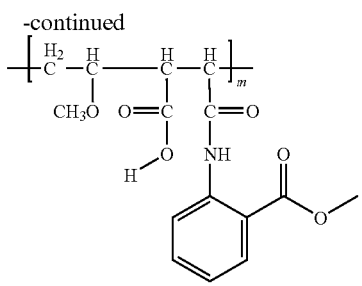

m is an integer greater than or equal to 1

In a 500 mL, 4-necked kettle equipped with a thermocouple, a Dean-Stark trap with condenser, a nitrogen purge adaptor, and a mechanical stirrer, 100 g of poly(methyl vinyl ether-co-maleic anhydride) copolymer (Gantrez® AN, International Specialty Products) in acetone solution (50% solids), 98 g of diisopropyl adipate (Ceraphyl® 230, International Specialty Products), 48 g of methyl-2-aminobenzoate were mixed and heated to reflux and acetone is removed. Then, the temperature was raised gradually from about 56° C. to 130° C. The mixture was maintained isothermally at 130° C. for 20 hours.

Polymer-Bound UV Absorber 2

Grafting UV-B Absorber onto poly(methyl vinyl ether-co-maleic anhydride)

In a 500-mL, 4-necked flask equipped with a thermocouple, a Dean-Stark trap with condenser, a nitrogen purge adaptor, and a mechanical stirrer, 100 g of poly(methyl vinyl ether-co-maleic anhydride) copolymer (Gantrez® AN, International Specialty Products) in acetone solution (50% solids), and 48 g of methyl 2-aminobenzoate are mixed and heated to reflux until the solution temperature reaches 80° C. The mixture temperature is kept isothermally at 80° C. for 6 hours.

Polymer-Bound UV Absorber 3

The process used to make Polymer-bound UV absorber 2 is repeated, except that the solution is heated to 100° C. and then maintained isothermally for 40 hours.

Polymer-Bound UV Absorber 4

Grafting UV-B Absorber onto poly(methyl vinyl ether-co-maleic anhydride)

In a 1-L, stainless high pressure reactor equipped with a thermocouple, a nitrogen purge adaptor, and a mechanical stirrer, 300 g of poly(methyl vinyl ether-co-maleic anhydride) copolymer (Gantrez® AN, International Specialty Products) in acetone solution (50% solids), and 72 g of methyl 2-aminobenzoate are mixed. The solution is purged with nitrogen at 50 psi and released to a pressure of 1 atmosphere three times. Then, the mixture is heated under pressure at 130° C.

The mixture temperature is kept isothermally at 130° C. for 20 hours. Then, the reactor is opened and acetone is removed.

Polymer-Bound UV Absorber 5

The method used to make Polymer-bound UV absorber 4 is repeated, except that the solution is heated to 170° C. and then maintained isothermally for 40 hours.

Example 1

Anti-Aging Cream

An anti-aging cream is created using a polymeric UV-B absorber (Table 2).

TABLE 2

Ingredients for anti-aging cream

| ingredient | amount (% w/w) | supplier |
|---|---|---|
| Phase A | | |
| deionized water | 61.96 | |
| disodium EDTA (Versene ™ NA) | 0.10 | Dow Chemical Company |
| acrylic acid/VP crosspolymer (UltraThix ™ P-100) | 0.90 | International Specialty Products |
| triethanolamine 99% | 0.06 | |
| Phase B | | |
| glycerin | 2.00 | |
| glyceryl polymethacrylate (and) propylene glycol (and) PVM/MV copolymer (Lubrajel ® Oil) | 2.00 | International Specialty Products |
| Phase C | | |
| triethanolamine 99% | 0.78 | |
| Phase D | | |
| myristyl myristate (Ceraphyl ® 424) | 2.60 | International Specialty Products |
| bis-PEG-12 dimethicone beeswax (Siliconyl Beeswax) | 1.50 | Koster Keunen, LLC |
| isocetyl stearoyl stearate (Ceraphyl ® 791) | 4.00 | International Specialty Products |
| isodecyl neopentanoate (Ceraphyl ® SLK) | 4.00 | International Specialty Products |
| glyceryl stearate (and) behenic alcohol (and) palmitic acid (and) stearic acid (and) lecithin (and) lauryl alcohol (and) myristyl alcohol (and) cetyl alcohol (ProLipid ® 141) | 4.00 | International Specialty Products |
| Polymer-bound UV absorber 4 | 5.00 | |
| Phase E | | |
| disodium lauriminodipropione tocopheryl phosphates (Vital ET ™) | 1.00 | International Specialty Products |
| caprylic/capric triglyceride (and) *Phoenix dactylifera* (date) seed extract (D'Orientine ™ S) | 2.50 | International Specialty Products |
| propylene glycol (and) diazolidinyl urea (and) methylparaben (and) propylparaben (Germaben ® II) | 1.00 | International Specialty Products |
| Phase F | | |
| nylon 12 (SP-500) | 1.00 | Kobo Products |
| mica (and) iron oxides (Cloisonne ® Super Bronze) | 2.00 | BASF Corp. |
| mica (and) iron oxides (Cloisonne ® Super Copper) | 0.60 | BASF Corp. |
| mica (and) titanium dioxide (and) iron oxides (Flamenco ® Twilight Gold) | 1.00 | BASF Corp. |
| silica (SB 700 Silica Beads) | 2.00 | US Cosmetics |
| TOTAL | 100.00 | |

Procedure:

1. Phase A water is heated to 70° C., disodium EDTA is added and mixed until uniform (propeller mixer).
2. UltraThix™ P-100 is sprinkled slowly into the back using propeller mixing.
3. Phase A aliquot of TEA is added and batch thickens slightly. The batch is mixed uniform.
4. Phase B is added to the batch, and mixed until uniform.
5. Phase C is added to batch using propeller mixing; batch thickens slightly. Batch is mixed until uniform.
6. Phase D is heated to 75° C.-80° C. and mixed until uniform. Then, Phase D is added to main batch using propeller mixing.
7. Transfer to homo-mixer and mix using moderate homo-mixing until uniform.
8. The batch is cooled with slow homo-mixing to 45° C. Phase E (Composition 4) is added and mixed until uniform.
9. Mixing is changed to sweep-mixing; and the batch is slowly cooled to room temperature.
10. Pre-pulverized Phase F is added to the batch while avoiding aeration. The entire batch is mixed until uniform.

Example 2

SPF-30 Spray Lotion

A sun care spray lotion is produced that contains a polymeric UV-B absorber (Table 3).

TABLE 3

Ingredients for a spray lotion

| ingredient | amount (% w/w) | supplier |
|---|---|---|
| Phase A | | |
| deionized water | 56.72 | |
| disodium EDTA (Versene ™ NA) | 0.10 | Dow Chemical Company |
| glycerin | 2.00 | |
| acrylic acid/VP crosspolymer (Ultrathix ™ P-100) | 0.30 | International Specialty Products |
| triethanolamine | 0.03 | |
| Phase B | | |
| avobenzone (Escalol ® 517) | 3.00 | International Specialty Products |
| octocrylene (Escalol ® 597) | 2.50 | International Specialty Products |
| octisalate (Escalol ® 587) | 5.00 | International Specialty Products |
| octinoxate (Escalol ® 557) | 5.00 | International Specialty Products |
| oxybenzone (Escalol ® 567) | 6.00 | International Specialty Products |
| Composition 5 | 5.00 | |
| glyceryl stearate (and) cetearyl alcohol (and) sodium stearoyl lactylate (Ritamulse SCG) | 1.25 | RITA Corporation |
| ceteareth-20 (Eumulgin ® B2) | 3.50 | Cognis GmbH |
| behenyl alcohol | 0.50 | International Specialty Products |
| isodecyl neopentanoate (Ceraphyl ® SLK) | 2.00 | International Specialty Products |
| C12-C15 alkyl lactate (Ceraphyl ® 41) | 4.00 | International Specialty Products |
| Phase C | | |
| triethanolamine | 0.20 | |
| Phase D | | |
| propylene glycol (and) diazolidinyl urea (and) methylparaben (and) propylparaben (Germaben ® II) | 0.80 | International Specialty Products |
| acrylates/C12-C22 alkyl methacrylate copolymer (Allianz ™ OPT) | 2.10 | International Specialty Products |
| TOTAL | 100.00 | |

Procedure:

1. UltraThix™ is dispersed into the water phase with rapid mixing.
2. The water phase is heated to 75° C.-80° C.
3. In a separate beaker, the oil phase is combined and heated to 70° C.-75° C.
4. The oil phase is added to the water phase.
5. The batch is mixed and cooling is started.
6. After the batch temperature is less than 45° C., the Allianz™ OPT and the Germaben® II are added.

The invention has been described in detail with particular reference to preferred embodiments thereof, but it will be understood that variations and modifications can be effected within the spirit and scope of the invention.

What is claimed is:

1. A personal care composition comprising from about 0.01% to 100% of a polymer-bound UV absorber comprising at least one unit having the structure:

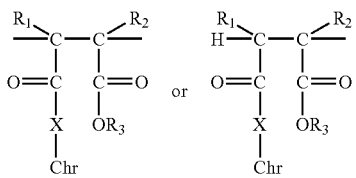

wherein:
(a) Chr-X is the residue of a UV absorber, wherein Chr is methyl-2-aminobenzoate and X is a constituent of said UV absorber and is selected from the group consisting of O and NH; (b) R1 and R2 are independently selected from the group consisting of: hydrogen, halogen atoms, alkyl groups, alkenyl groups, cycloalkyl groups, and aryl groups; (c) R3 is selected from the group consisting of: hydrogen, metal atoms, and organic amine groups; and (d) wherein C— indicates a covalent bond to a polymer backbone or side chain; and wherein the composition further comprises at least one cosmetic or pharmaceutical ingredient selected from the group comprising: actives, anti-oxidants, colorants, defoamers, emollients, fragrances, humectants, labile UV absorbers, lower monoalcohols, lower polyols, oils, pigments, preservatives, propellants, surfactants, thickeners, UV absorbers, waxes, and blends thereof, and is in the form of an aerosol, conditioner, cream, dispersion, emulsion, foundation, gel, lotion, mist, moisturizer, mousse, paste, powder, roll-on, shampoo, stick, spray, suspension, or wipe.

2. The personal care composition of claim 1 wherein said UV-absorbing polymer comprises at least one unit having the structure:

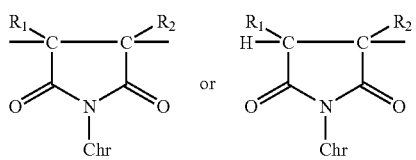

wherein
(a)

is the residue of a UV absorber; (b) R1 and R2 are independently selected from the group consisting of: hydrogen, halogen atoms, alkyl groups, alkenyl groups, cycloalkyl groups, and aryl groups, and (c) wherein C— indicates a covalently bonded to a polymer backbone or side chain.

3. The composition of claim 1 or 2 wherein said unit having the structure:

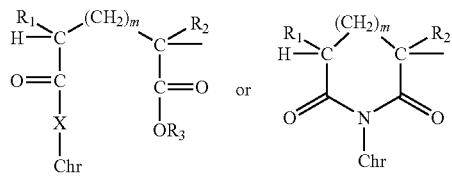

occurs pendant to the polymer backbone.

4. The composition of claim 3 wherein said polymer backbone is derived from a polymer selected from the group consisting of: homopolymers and non-homopolymers of polybutadienes and polyisoprenes.

5. The composition of claim 1 wherein said unit having the structure:

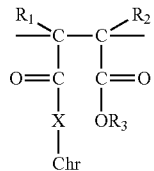

comprises all or part of the polymer backbone.

6. The composition of claim 5 wherein said polymer backbone is derived from a polymer selected from the group consisting of: homopolymer, copolymers, and non-homopolymers of: maleic anhydride, methyl maleic anhydride, dimethyl maleic anhydride, and halogenated analogues thereof.

7. The composition of claim 6 wherein said copolymers comprise repeating units selected from the group consisting of: alkylacrylamides including acrylamide and methacrylamide, acrylates, allyl derivatives, benzoxanes, cinnamyls, epoxides, fumarates, maleates, maleimides, oxazolines, oxetanes, styrenes, vinyl acetates, vinyl acrylamides, vinyl carbonates, vinyl ethers, vinyl imidazoles, vinyl triazoles, vinyl lactams, vinyl pyridines, vinyl silanes, vinyl sulfones, and mixtures thereof.

8. The composition of claim 1 or 2 wherein said polymer-bound UV absorber has a molecular weight from about 200 amu to about 5,000,000 amu.

9. The composition of claim 1 or 2 wherein said polymer-bound UV absorber further comprises an additional UV absorber selected from the group consisting of: aminobenzoic acid; 2-aminobenzophenone; amyl dimethyl PABA; bemotrizinol; benzophenone-3; benzophenone-4; benzophenone-9; 2-(2H-benzotriazole-2-yl)-4,6-di-tert-pentylphenol; 2-(2H-benzotriazole-2-yl)-4-methylphenol; 2-(2H-benzotriazole-2-yl)-4,6-bis(1-methyl-1-phenylethyl)phenol; bisbenzoxazoyl phenyl ethylhexyl amino triazine; 3-benzylidene camphor sulfonic acid; CAS number 152261-33-1; N,N'-bisformyl-N,N'-bis-(2,2,6,6-tetramethyl-4-piperidinyl)-hexamethylendiamine; bisoctrizole; 2-[(p-(tert-butylamido)-anilino]-4,6,-bis[(p-(2'-ethylhexyl-1'-oxycarbonyl)-anilino]-1,3,5-triazine; 6-tert-butyl-2-(5-chloro-2Hbenzotriazole-2-yl)-4-methylphenol; 2,4-di-tert-butyl-6-(5-chloro-2H-benzotriazole-2-yl)phenol; camphor benzalkonium methosulfate; diethanolamine p-methoxycinnamate; diethylaminohydroxybenzoylhexylbenzoate; diethylhexyl butamido triazone; digalloyl trioleate; dioxybenzone; disodium phenyl dibenzimidazole tetrasulfonate; drometrizole trisiloxane; ecamsule; ensulizole; ethyl 4-bis(hydroxypropyl)aminobenzoate; ethylhexyl pmethoxycinnamate; 2-ethylhexyl salicylate; ethylhexyl triazone; beta-2-glucopyranoxypropylhydroxybenzophenone; glyceryl aminobenzoate; homomenthyl salicylate; [2-hydroxy-4-(octyloxy)pheny 1](phenyl)methanone; 2-[bis(2-hydroxyethyl)amino]ethyl salicylate; (E)-3-(4-hydroxy-3-methoxyphenyl)prop-2-enoic acid; lawsone with dihydroxyacetone; meradimate; methoxycinnamido propyl hydroxy sultaine menthyl anthranilate; meradimate; methyl-2-aminobenzoate; oxybenzone; 2-phenylbenzimidazole-5-sulfonic acid (and its potassium, sodium and triethanolamine salts); sulisobenzone; bis-(2,2,6,6-tetramethyl-4-piperidyl)-sebacate; sterically hindered oligomeric amine, triethanolamine salicylate, and blends thereof.

10. The composition of claim 9 wherein said polymer-bound UV absorber comprises more than one UV absorber.

11. The personal care composition of claim 1 that is water-resistant or water-proof.

12. A personal care composition comprising from about 0.01% to 100% of a polymer-bound UV absorber comprising at least one unit having the structure:

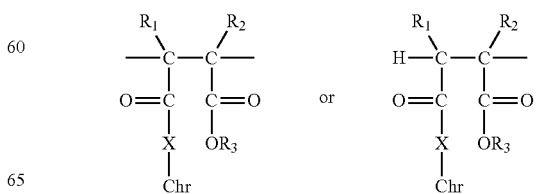

wherein:
(a) Chr-X is the residue of a UV absorber, wherein Chr is methyl-2-aminobenzoate and X is NH; (b) R1 and R2 are hydrogen; (c) R3 is hydrogen; and (d) wherein C— indicates a covalent bond to a polymer backbone or side chain; and wherein the composition further comprises at least one cosmetic or pharmaceutical ingredient selected from the group comprising: actives, anti-oxidants, colorants, defoamers, emollients, fragrances, humectants, labile UV absorbers, lower monoalcohols, lower polyols, oils, pigments, preservatives, propellants, surfactants, thickeners, UV absorbers, waxes, and blends thereof, and is in the form of an aerosol, conditioner, cream, dispersion, emulsion, foundation, gel, lotion, mist, moisturizer, mousse, paste, powder, roll-on, shampoo, stick, spray, suspension, or wipe.

* * * * *